United States Patent
Ankersmit

(10) Patent No.: US 8,415,112 B2
(45) Date of Patent: Apr. 9, 2013

(54) COPD DIAGNOSIS

(75) Inventor: Jan Hendrik Ankersmit, Vienna (AT)

(73) Assignee: Aposcience AG, Vienna (AT)

( * ) Notice: Subject to any disclaimer, the term of this patent is extended or adjusted under 35 U.S.C. 154(b) by 0 days.

(21) Appl. No.: 12/999,291

(22) PCT Filed: Jul. 2, 2009

(86) PCT No.: PCT/EP2009/058357
§ 371 (c)(1),
(2), (4) Date: Dec. 15, 2010

(87) PCT Pub. No.: WO2010/000820
PCT Pub. Date: Jan. 7, 2010

(65) Prior Publication Data
US 2011/0097752 A1    Apr. 28, 2011

(30) Foreign Application Priority Data
Jul. 2, 2008    (EP) .................................... 08450098

(51) Int. Cl.
*G01N 33/53* (2006.01)
*G01N 31/00* (2006.01)

(52) U.S. Cl.
USPC ........... 435/7.21; 435/7.1; 436/501; 436/518; 424/9.1; 424/520; 530/300; 530/350

(58) Field of Classification Search .................. None
See application file for complete search history.

(56) References Cited

FOREIGN PATENT DOCUMENTS

| EP | 1394274 | 3/2004 |
|---|---|---|
| WO | 0073803 | 12/2000 |
| WO | 2004070058 | 8/2004 |
| WO | 2006105252 | 10/2006 |
| WO | 2006118522 | 11/2006 |
| WO | 2007127749 | 11/2007 |
| WO | 2007131031 | 11/2007 |

OTHER PUBLICATIONS

Aigner, C., et al., "Locally advanced non-small-cell lung cancer (NSCLC)—do intrapulmonary satellite nodules fit in this category?", Wiener Klinische Wochenschrift, The Middle European Journal of Medicine (2008) 120/13-14: A13-A35.
Bolton, C.E, et al., "Attaining a Correct Diagnosis of COPD in General Practice", Respiratory Medicine, 2005, 99, 493-500, Elsevier Ltd., UK.
Brown, Aaron M., et al., "ST2 in Emergency Department Chest Pain Patients with Potential Acute Coronary Syndromes", Annals of Emercengy Medine, 2007, 153-158.
Eaton, Tam, et al., "Spitometry in Primary Care Practice: The Importance of Quality Assurance and the Impact of Spirometry Workshops", Chest, Official Publication of the American College of Chest Physicians,1999, 416-423.
Greystone, A., et al., "Optimisation of Circulating Biomarkers of Cell Death for Routine Clinical Use", Annals of Oncology, 2008, 19:990-995.
Harnoncourt, K., et al., "Die Standardisierung der Lungenfunktionsdiagnostik in Osterreich", Osterreichische Arztezeitung, 1982, 1640-1642.
Henson, P.M., et al., "Apoptpsis in the Lung: Induction, Clearance and Detection", Am J Physical Lung Cell Mol Physiol, 2008.
Higenbottam, T., et al., "Lung Function and Symptoms of Cigarette Smokers Related to Tar Yield and Number of Cigarettes Smoked", Drugs and Society, 1980, 409-411.
Hodge, S., et al., "Increase airway epithelial and T-cell apoptosis in COPD remains despite smoking cessation", Eu Respir J, (2005) 25: 447-454.
Kohler, G., et al., "Continuous cultures of fused cells secreting antibody of predefined specificity", Nature, (1975) 256:495-497.
Quanjer, et al., "Lung Volumes and Forced Ventilatory Flows", European Respiratory Journal, (1993) 6/16:5-40.
Rumora, et al., "Reduction in Peripheral Blood Leukocyte Heat Shock Proteins 27 and 70 Expression in Chronic Obstructive Pulmonary Disease", Croatica Chemica ACTA, (2007) 73-80.
Schermer, T.R., et al., "Validity of spirometric testing in a general practice population of patients with chronic obstructive pulmonary disease (COPD)", Thorax, (2003) 58:861-866.
Ulukaya, E. et al., "The levels of caspase-cleaved cytokeratin 18 are elevated in serum from patients with lung cancer and helpful to predict the survival", Lung Cancer (2007) 56:399-404.
Wien Klin Wochenschr (2008) 120/13-14: A13-A35.

*Primary Examiner* — Lisa Cook
(74) *Attorney, Agent, or Firm* — Chainey P. Singleton; Edwin S. Flores; Chalker Flores, LLP

(57) ABSTRACT

The present invention relates to a method for diagnosing chronic obstructive pulmonary disease (COPD) in a human subject or the risk of a human subject to develop COPD comprising the steps of: —providing a sample from a human subject, —determining the amount of caspase-cleaved cytokeratin-18 (ccCK-18), histones, heat shock protein 27 (HSP27), heat shock protein 70 (HSP70) and/or heat shock protein 90 alpha (HSP90 alpha) in said sample, —diagnosing COPD when the amount of ccCK-18, histones, HSP27, HSP70 and/or HSP90 alpha is increased compared to the amount of ccCK-18, histones, HSP27, HSP70 and/or HSP90 alpha in healthy human subjects, or—diagnosing the risk to develop COPD when the amount of ccCK-18, histones and/or HSP70 is reduced compared to the amount of ccCK-18, histones and/or HSP70 in healthy human subjects.

15 Claims, 20 Drawing Sheets

COPD DIAGNOSIS

The present invention relates to methods for diagnosing COPD in a human subject.

Chronic Obstructive Pulmonary Disease (COPD) is one of the leading causes of death worldwide. In 2020, only ischemic heart disease and cerebrovascular disease will account for a higher mortality among the world's population. Prevalence and hospitalization rates have inclined dramatically over the past years. Several studies have shown a strong correlation between tobacco smoking and the development of COPD although not every smoker develops the clinical features of COPD (Higenbottam T et al. (1980) Lancet 315:409-411). The pathogenesis is characterized by airflow obstruction due to airway remodelling and aberrant inflammation. COPD comprises chronic bronchitis and emphysema, both conditions characterized by tissue destruction. Airflow limitation is slowly progressive, leading to dyspnoea and limitations of physical exercise capacities. However, impairment is not restricted to the lungs, as COPD patients are also at higher risk for systemic failures including cardiovascular diseases. Diagnosis of airway obstruction according to the guidelines of the Global Initiative for Chronic Obstructive Lung Diseases (GOLD) requires the use of spirometry. A postbronchodilator FEV1/FVC (forced expiratory volume in one second/forced vital capacity) ratio of less than 70% indicates an irreversible airflow obstruction, and is therefore considered to be the main parameter for the diagnosis of COPD (Global Strategy for Diagnosis, Management, and Prevention of COPD. Global Initiative FOR Chronic Obstructive Lung Disease, 2007, www.goldcopd.com). Currently, patients are classified into GOLD stages according to spirometry data and clinical presentation. The detection of serum markers indicating disease activity is of special interest in the diagnostic and therapeutic process.

Although smoking is widely accepted as the major risk factor for the development of COPD, descriptions of specific pathogenic pathway and involved mechanisms remain vague. Oxidative stress on lung parenchyma seems to be involved in initiating the inflammatory response to tobacco smoke exposure. Neutrophils and macrophages, as part of the innate immunity, were considered pivotal in the airway remodelling process in COPD. This remodelling process is a consequence of chronic apoptosis induction in lungs of patients with COPD or smokers. Apoptosis refers to the morphological alteration exhibited by "actively" dying cells including cell shrinkage, membrane blebbing, chromatin condensation and DNA fragmentation. Apoptosis includes alveolar and bronchial epithelial cells as well as endothelial cells in the parenchyma. Controlled apoptosis is a wanted process and critical to cellular homeostasis. However, excessive triggering of apoptosis and increased turnover of alveolar cells may lead to tissue destruction.

Immunohistochemical observations in lung tissue derived from COPD patients revealed inflammatory infiltrates, composed of T lymphocytes and macrophages, with variable numbers of mast cells, neutrophils, and eosinophils. Advances in immune reactions have shown that an imbalance between T-helper type 1 (TH1) and T-helper type 2 (TH2) cells plays a role in the inflammatory response of various diseases. Studies have revealed a predominant TH1 cytokine pattern in the infiltrating interstitial inflammation in COPD. The airway epithelium is a critical component of the immune reaction, producing pro-inflammatory cytokines—including tumor-necrosis-factor alpha (TNFα) and interleukin-1 beta (IL-1β)—and chemokines. Epithelial cells of the lung also modulate acute exacerbations and reactions to pathogens that are common in patients suffering from COPD.

The only method used in the clinical practice for diagnosing COPD is spirometry, which is a pulmonary function test measuring lung function, specifically the measuring of the amount (volume) and/or speed (flow) of air that can be inhaled and exhaled. However, such tests are also used to diagnose other pulmonary diseases like asthma and pulmonary fibrosis. Therefore, such a method cannot function as the sole test to reliable diagnose COPD. Therefore, the physicians consider also symptoms like dyspnea, chronic cough or sputum production, and/or a history of exposure to risk factors for diagnosing COPD. It is evident that the use of such methods in diagnosing COPD or in discriminating various forms of COPD may result in a false diagnosis, so that the patient cannot utilise the best form of therapy right from the beginning of the disease.

Therefore, it is an object of the present invention to provide methods and means which allow for unequivocally diagnosing COPD in a human subject from the beginning of the disease or even for determining the risk of a human subject to develop COPD.

The present invention relates to a method for diagnosing chronic obstructive pulmonary disease (COPD) in a human subject or the risk of a human subject to develop COPD comprising the steps of:

providing a sample from a human subject, determining the amount of caspase-cleaved cytokeratin-18 (ccCK-18), histones, heat shock protein 27 (HSP27), heat shock protein 70 (HSP70) and/or heat shock protein 90 alpha (HSP90 alpha) in said sample, diagnosing COPD when the amount of ccCK-18, histones, HSP27, HSP70 and/or HSP90 alpha is increased compared to the amount of ccCK-18, histones, HSP27, HSP70 and/or HSP90 alpha in healthy human subjects, or diagnosing the risk to develop COPD when the amount of ccCK-18, histones and/or HSP70 is reduced compared to the amount of ccCK-18, histones and/or HSP70 in healthy human subjects.

It turned out that the concentration of ccCK-18, histones, HSP27, HSP70 and/or HSP90 alpha in a sample of a human can function as marker which allows to diagnose COPD, in particular COPD stages I/II and III/IV in said human subject. The markers even allow to determine the risk of a human subject to develop COPD in the future. Not all humans which are considered as being at risk to develop COPD due to their lifestyle (e.g. humans subjected to smoke, smokers etc.) will come down with COPD. Therefore, the diagnosis that a human subject is at risk to develop COPD is very useful in the prevention of COPD.

The markers used in the method of the present invention may be used singularly or in combination, whereby further the amount of interleukin-1 receptor 4 (ST2) may be determined, wherein COPD is diagnosed when the amount of ST2 is increased compared to the amount of ST2 in healthy human subjects or wherein the risk to develop COPD is diagnosed when the amount of ST2 is reduced compared to the amount of ST2 in healthy human subjects. Preferred combinations involve ST2 and ccCK-18, ST2 and histones, ccCK-18 and histones, ST2, HSP27, HSP70 and/or HSP90 alpha.

In order to classify the severity of COPD spirometric parameters are used. These parameters allow to classify the severity of COPD into four stages (see Table A). Spirometry is essential for diagnosis and provides a useful description of the severity of pathological changes in COPD. Specific spirometric cut-points (e.g., post-bronchodilator $FEV_1/FVC$ ratio<0.70 or $FEV_1$<80, 50, or 30% predicted) are used to determine the COPD stages I to IV.

TABLE A

Spirometric Classification of COPD (according to www.goldcopd.com). Severity Based on Post-Bronchodilator $FEV_1$.

| Stage I: Mild | $FEV_1/FVC < 0.70$ |
| --- | --- |
| | $FEV_1$ 80% predicted |
| Stage II: Moderate | $FEV_1/FVC < 0.70$ |
| | 50% $FEV_1 < 80\%$ predicted |
| Stage III: Severe | $FEV_1/FVC < 0.70$ |
| | 30% $FEV_1 < 50\%$ predicted |
| Stage IV: Very Severe | $FEV_1/FVC < 0.70$ |
| | $FEV_1 < 30\%$ predicted or $FEV_1 < 50\%$ predicted plus chronic respiratory failure |

$FEV_1$: forced expiratory volume in one second;
FVC: forced vital capacity;
respiratory failure: arterial partial pressure of oxygen ($PaO_2$) less than 8.0 kPa (60 mm Hg) with or without arterial partial pressure of $CO_2$ ($PaCO_2$) greater than 6.7 kPa (50 mm Hg) while breathing air at sea level.

Methods for determining $FEV_1$ and FVC, which can be used to systematise COPD (see Table A), are well-known in the art (see e.g. Eaton T, et al. Chest (1999) 116:416-23; Schermer T R, et al. Thorax (2003) 58:861-6; Bolton C E, et al. Respir Med (2005) 99:493-500).

The impact of COPD on an individual patient depends not just on the degree of airflow limitation, but also on the severity of symptoms (especially breathlessness and decreased exercise capacity). There is only an imperfect relationship between the degree of airflow limitation and the presence of symptoms. The characteristic symptoms of COPD are chronic and progressive dyspnea, cough, and sputum production. Chronic cough and sputum production may precede the development of airflow limitation by many years. This pattern offers a unique opportunity to identify smokers and others at risk for COPD, and intervene when the disease is not yet a major health problem.

Conversely, significant airflow limitation may develop without chronic cough and sputum production. Although COPD is defined on the basis of airflow limitation, in practice the decision to seek medical help (and so permit the diagnosis to be made) is normally determined by the impact of a particular symptom on a patient's lifestyle.

Stage I: Mild COPD—Characterized by mild airflow limitation ($FEV_1/FVC<0.70$; $FEV_1$ 80% predicted). Symptoms of chronic cough and sputum production may be present, but not always. At this stage, the individual is usually unaware that his or her lung function is abnormal.

Stage II: Moderate COPD—Characterized by worsening airflow limitation ($FEV_1/FVC<0.70$; 50% $FEV_1<80\%$ predicted), with shortness of breath typically developing on exertion and cough and sputum production sometimes also present. This is the stage at which patients typically seek medical attention because of chronic respiratory symptoms or an exacerbation of their disease.

Stage III: Severe COPD—Characterized by further worsening of airflow limitation ($FEV_1/FVC<0.70$; 30% $FEV_1<50\%$ predicted), greater shortness of breath, reduced exercise capacity, fatigue, and repeated exacerbations that almost always have an impact on patients' quality of life.

Stage IV: Very Severe COPD—Characterized by severe airflow limitation ($FEV_1/FVC<0.70$; $FEV_1<30\%$ predicted or $FEV_1<50\%$ predicted plus the presence of chronic respiratory failure). Respiratory failure is defined as an arterial partial pressure of $O_2$ ($PaO_2$) less than 8.0 kPa (60 mm Hg), with or without arterial partial pressure of $CO_2$ ($PaCO_2$) greater than 6.7 kPa (50 mm Hg) while breathing air at sea level. Respiratory failure may also lead to effects on the heart such as cor pulmonale (right heart failure). Clinical signs of cor pulmonale include elevation of the jugular venous pressure and pitting ankle edema. Patients may have Stage IV: Very Severe COPD even if the $FEV_1$ is >30% predicted, whenever these complications are present. At this stage, quality of life is very appreciably impaired and exacerbations may be life threatening.

The term "at risk to develop COPD", as used herein, refers to a pool of human subjects which are subjected to environmental threats or which may have a genetic predisposition to develop COPD. Factors which support the formation of COPD include genetic predisposition, exposure to particles like tobacco smoke, occupational dusts (organic and inorganic), indoor air pollution from heating and cooking with biomass in poorly vented dwellings and outdoor air pollution, lung growth and development, oxidative stress, gender, age, respiratory infections, socioeconomic status, nutrition and comorbidities. Humans which are at risk to develop COPD may suffer from chronic cough, chronic sputum production and normal spirometry. However, human subjects suffering from these symptoms do necessarily progress on to COPD stage I.

As used herein, the term "healthy human subject" refers to humans which do not suffer from COPD or any other pulmonary disease. Furthermore, these humans did not have any severe pulmonary disease in their life. "Healthy humans" do also not include humans which are regularly exposed to risk factors, like smoke or other noxious substances.

According to the present invention the amount of the markers in "healthy human subjects" is determined by quantifying these markers in at least 5, 10, 15, or 20 "healthy human subjects".

Since the COPD markers determined with the method according to the present invention are found in blood, the sample to be used according to the present invention is blood, serum or plasma. These type of samples can be obtained from a human with methods known in the art.

In order to specifically determine the amount of interleukin-1 receptor 4 (ST2), caspase-cleaved cytokeratin-18 (ccCK-18) and histones, heat shock protein 27 (HSP27), heat shock protein (HSP70) and/or heat shock protein 90 alpha (HSP90 alpha) in a sample it is preferred to use methods which involve antibodies directed to said COPD markers. Suitable methods using antibodies are immunoassays which are preferably selected from the group consisting of enzyme-linked immunosorbent assay (ELISA), radioimmunoassay (RIA) and Western Blot.

The term "antibody", as used herein, refers to monoclonal and polyclonal antibodies or fragments thereof capable to bind to an antigen. Other antibodies and antibody fragments, such as recombinant antibodies, chimeric antibodies, humanized antibodies, antibody fragments such as Fab or Fv fragments, as well as fragments selected by screening phage display libraries, and the like are also useful in the methods described herein.

Methods for preparation of monoclonal as well as polyclonal antibodies are well established (Harlow E. et ah, 1988. Antibodies. New York: Cold Spring Harbour Laboratory). Polyclonal antibodies are raised in various species including but not limited to mouse, rat, rabbit, goat, sheep, donkey, camel and horse, using standard immunization and bleeding procedures. Animal bleeds with high titres are fractionated by routine selective salt-out procedures, such as precipitation with ammonium sulfate and specific immunoglobulin fractions being separated by successive affinity chromatography on Protein-A-Sepharose and leptin-Sepharose columns, according to standard methods. The purified polyclonal as well as monoclonal antibodies are then characterised for specificity. Such characterization is performed by standard methods using proteins labeled with a tracer such as a radio-isotope or biotin in competition with increasing levels of unlabeled potential cross-reactants for antibody binding. Binding studies are further evaluated by other standard methods such as the well-established sodium dodecyl sulphate-polyacrylamide gel electrophoresis (SDS-PAGE) and Western immunoblot methods under reducing and non-reducing conditions.

Monoclonal antibodies are prepared according to well established standard laboratory procedures ("Practice and Theory of Enzyme Immunoassays" by P. Tijssen (hi Laboratory Techniques in Biochemistry and Molecular Biology, Eds: R. H. Burdon and P. H. van Kinppenberg; Elsevier Publishers Biomedical Division, 1985)), which are based on the original technique of Kohler and Milstein (Kohler G., Milstein C. Nature 256:495, 1975). This technique is performed by removing spleen cells from immunized animals and immortalizing the antibody producing cells by fusion with myeloma cells or by Epstein-Barr virus transformation, and then screening for clones expressing the desired antibody, although other techniques known in the art are also used. Antibodies are also produced by other approaches known to those skilled in the art, including but not limited to immunization with specific DNA.

Preferably used immunoassays are based on techniques which use capture antibodies, which are able to specifically bind to an antigen of interest, or antigens bound on a solid support. The capture antibody is coupled with or linked to various solid phase supports using standard non-covalent or covalent binding methods, depending on the required analytical and/or solid-phase separation requirements. The solid-support is in the form of test tubes, beads, microparticles, filter paper, membranes, glass filters, magnetic particles, glass or silicon chips or other materials and approaches known to those skilled in the art. The use of microparticles, particularly magnetizable particles, that have been directly coated with the antibody (magnetic particles-capture antibody) or particles that have been labelled with a universal binder (e.g., avidin or anti-species antibody) is useful for significantly shortening the assay incubation time. These along with other alternative approaches known in the art allow for assay completion within minutes without limiting the required sensitivity.

The detection antibody, which is able to specifically bind to the antigen of interest, used for detection of the antigen is either directly coupled with a reporter molecule, or detected indirectly by a secondary detection system. The latter is based on several different principles known in the art, including antibody recognition by a labelled anti-species antibody and other forms of immunological or non-immunological bridging and signal amplification detection systems (e.g., the biotin-streptavidin technology). The signal amplification approach is used to significantly increase the assay sensitivity and low level reproducibility and performance. The label used for direct or indirect antibody coupling is any detectable reporter molecule. Examples of suitable labels are those widely used in the field of immunological and non-immunological detection systems, such as fluorophores, luminescent labels, metal complexes and radioactive labels, as well as moieties that could be detected by other suitable reagents such as enzymes, or various combinations of direct or indirect labels such as enzymes with luminogenic substrates.

In order to diagnose COPD or the risk to develop COPD it is advantageous to define cut-off levels above or beneath which the disease can be diagnosed. The amount of interleukin-1 receptor 4 (ST2) in blood samples of a healthy human subject ranges preferably from 50 to 150 pg/ml, preferably 60 to 140 pg/ml, more preferably 70 to 130 pg/ml.

According to another embodiment of the present invention the amount of caspase-cleaved cytokeratin-18 (ccCK-18) in blood samples of a healthy human subject ranges from 200 to 350 U/l, preferably from 200 to 330 U/l, more preferably from 250 to 300 U/l, measured as cytokeratin-18 new epitope M30.

According to another embodiment of the present invention the amount of heat shock protein 27 (HSP27), in blood samples of a healthy human subject ranges from 1500 to 2500 pg/ml, preferably from 1600 to 2400 pg/ml, more preferably from 1700 to 2300 pg/ml.

According to another embodiment of the present invention the amount of heat shock protein 70 (HSP70) in a blood samples of a healthy human subject ranges from 50 to 200 pg/ml, preferably from 70 to 190 pg/ml, more preferably from 80 to 180 pg/ml.

According to another embodiment of the present invention the amount of heat shock protein 90 alpha (HSP90 alpha) in a blood samples of a healthy human subject ranges from 10,000 to 15,000 pg/ml, preferably from 11,000 to 14,500 pg/ml, more preferably from 12,000 to 14,000 pg/ml.

According to a further embodiment of the present invention the amount of histones in blood samples of a healthy human subject is 20 to 50% lower, preferably 25 to 40% lower, than in blood samples of a human subject suffering from COPD.

According to a preferred embodiment of the present invention COPD is diagnosed when the amount of interleukin-1 receptor 4 (ST2), caspase-cleaved cytokeratin-18 (ccCK-18), histones, HSP27, HSP70 and/or HSP90 alpha in the sample is at least 10%, preferably at least 20%, increased compared to the amount of ST2, ccCK-18, histones, HSP27, HSP70 and/or HSP90 alpha in healthy human subjects. Of course the amount of ST2, ccCK-18, histones, HSP27, HSP70 and/or HSP90 alpha may also be increased by at least 15%, 25%, 30%, 40%, 50%, 60%, 70%, 80%, 90% or 100%.

The risk to develop COPD is preferably diagnosed when the amount of interleukin-1 receptor 4 (ST2), caspase-cleaved cytokeratin-18 (ccCK-18) and/or histones in the sample is at least 10%, preferably at least 20%, reduced compared to the amount of ST2, ccCK-18 and/or histones in healthy human subjects. Of course the amount of ST2, ccCK-18 and/or histones may also be decreased by at least 15%, 25%, 30%, 40%, 50%, 60%, 70%, 80%, 90% or 100%.

The method according to the present invention is applicable also for other kind of mammals whereby the mammal is preferably selected from the group consisting of horse, dog, cat and cattle.

Another aspect of the present invention relates to a method for discriminating between COPD stage I/II and COPD stage III/IV in a human subject comprising the steps of:
  providing a sample from a human subject suffering from COPD,
  determining the amount of caspase-cleaved cytokeratin-18 (ccCK-18), histones, heat shock protein 27 (HSP27) and/or heat shock protein 70 (HSP70) in said sample,
  diagnosing COPD stage I/II when the amount of ccCK-18, histones, and/or HSP27 is reduced compared to the amount of ccCK-18, histones and/or HSP27 determined in a sample from a human subject suffering from COPD stage III/IV and/or when the amount of HSP70 is increased compared to the amount of HSP70 determined in a sample from a human subject suffering from COPD stage III/IV, or diagnosing COPD stage III/IV when the amount of ccCK-18, histones and/or HSP27 is increased compared to the amount of ccCK-18, histones and/or HSP27 determined in a sample from a human subject suffering from COPD stage I/II and/or when the amount of HSP70 is reduced compared to the amount of HSP70 determined in a sample from a human subject suffering from COPD stage I/II.

According to a preferred embodiment of the present invention the amount of interleukin-1 receptor 4 (ST2) is further determined, wherein COPD stage I/II is diagnosed when the amount of ST2 is increased compared to the amount of ST2 determined in a sample from a human subject suffering from COPD stage III/IV, or wherein COPD stage III/IV is diagnosed when the amount of ST2 is reduced compared to the amount of ST2 determined in a sample from a human subject suffering from COPD stage I/II.

The COPD markers disclosed herein are also suited to discriminate between humans suffering from COPD stage I/II and COPD stage III/IV as defined above. The discrimination between these COPD stages is important to determine the therapy. For patients with few or intermittent symptoms (stage I and II), for instance, use of a short-acting inhaled bronchodilator as needed to control dyspnea is sufficient. If inhaled bronchodilators are not available, regular treatment with slow-release theophylline should be considered. In humans whose dyspnea during daily activities is not relieved despite treatment with as-needed shortacting bronchodilators, adding regular treatment with a long-acting inhaled bronchodilator is recommended. In humans suffering COPD stages III/IV regular treatment with inhaled glucocorticosteroids reduces the frequency of exacerbations and improves health status. In these humans, regular treatment with an inhaled glucocorticosteroid should be added to long-acting inhaled bronchodilators. For humans suffering from COPD stage III/IV surgical treatments and/or long term oxygen should be considered if chronic respiratory failure occurs.

The reference values which allow to discriminate between COPD stages I/II and III/IV can be assessed by determining the respective amounts of ST2, ccCK-18, histones, HSP27 and/or HSP70 in a pool of samples obtained from humans suffering COPD stages I/II and III/IV. Such a pool may comprise samples obtained from at least 5, preferably at least 10, more preferably at least 20, humans suffering from COPD and for which the various COPD stages have been diagnosed by alternative methods (e.g. spirometry).

COPD I/II can be diagnosed in a human subject when the amount of HSP27 in a sample of said subject ranges between 2,600 and 3,300 pg/ml, preferably between 2,700 and 3,200 pg/ml. If the amount of HSP27 in a sample of a human subject ranges between 3,400 and 5,500 pg/ml, preferably between 3,500 and 5,000 pg/ml, more preferably between 3,600 and 4,500 pg/ml COPD III/IV is diagnosed.

COPD I/II can be diagnosed in a human subject when the amount of ST2, a sample of said subject ranges between 160 and 400 pg/ml, preferably between 170 and 380 pg/ml, more preferably between 180 and 350 pg/ml. COPD I/II can further be diagnosed when the amount of ST2 in more than 160, preferably more than 170, more preferably more than 180 pg/ml in said sample.

COPD I/II and COPD III/IV can be diagnosed when the amount of HSP70 in a sample of human subject is at least 250 pg/ml, preferably at last 300 pg/ml.

COPD I/II and COPD III/IV can be diagnosed when the amount of HSP90alpha in a sample of human subject is at least 15,000 pg/ml, preferably at least 16,000 pg/ml.

Another aspect of the present invention relates to a method for monitoring the progress of chronic obstructive pulmonary disease (COPD) in a human subject comprising the steps of:
providing a sample from a human subject,
determining the amount of caspase-cleaved cytokeratin-18 (ccCK-18), histones, heat shock protein 27 (HSP27) and/or heat shock protein 70 (HSP70) in said sample,
comparing the amount of ccCK-18, histones, HSP27 and/or HSP70 in the sample of said human subject with the amount of ccCK-18, histones, HSP27 and/or HSP70 in a sample from said human subject determined in an earlier sample of said human subject.

The markers disclosed herein can also be used to monitor the progress of COPD and the progress of a COPD therapy. Such a method involves the comparison of the amount of ccCK-18, histones, HSP27 and/or HSP70 in samples obtained from a human at different time intervals. The results obtained from said method allow the physician to set an appropriate therapy.

The present invention is further illustrated by the following figures and examples, however, without being restricted thereto.

Figure 5:
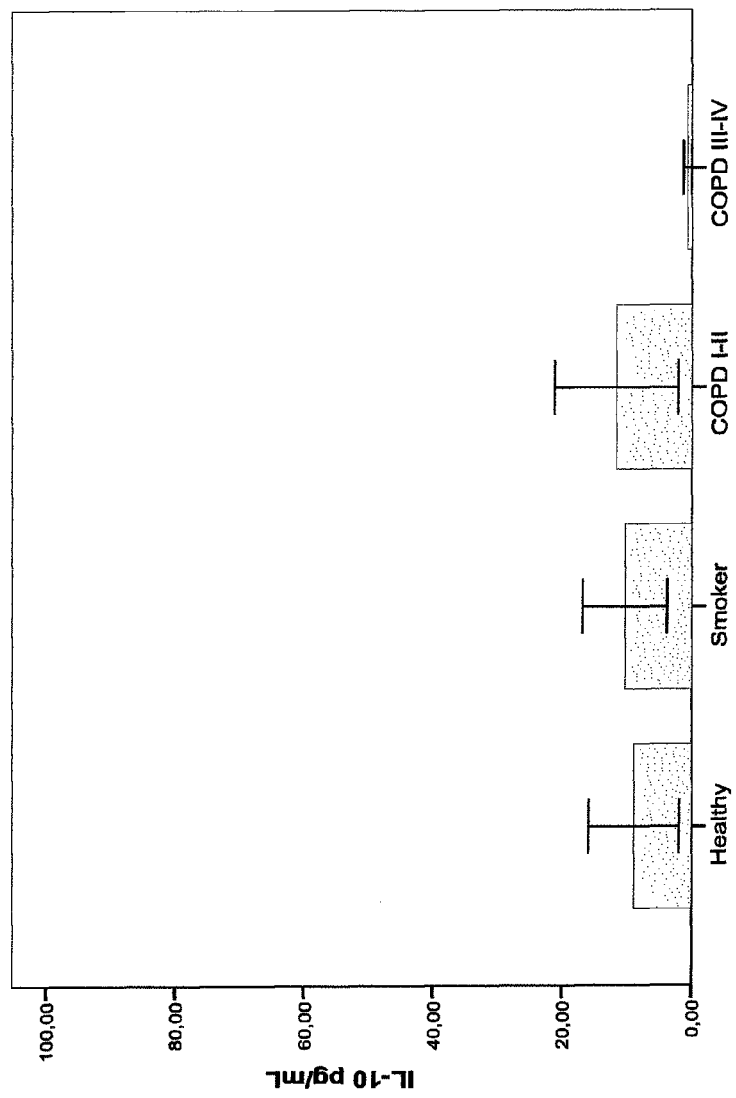

FIG. 5 indicates that IL-10 in serum samples showed no difference between the study groups (+/−SEM).

FIG. 6 shows the correlations between serum concentrations of ICE and number of patients' pack years (A), circulating histone-associated-DNA-fragments and serum ICE levels (B), FEV1% VC and serum caspase-cleaved cytokeratin-18 (C), and anti-inflammatory markers ST2 and IL-10 (D), respectively. R—spearman's rank correlation coefficient.

FIG. 7 (*a, b, c, d, e, f*) show serum levels of heat shock proteins and 20S proteasomes determined in the systemic blood flow of patients and controls. Results are expressed as mean +/−SEM.

FIGS. 8*a* to 8*d* show non-parametric correlations between HSP27, HSP70 and inflammatory cytokine IL-6 and lung function parameter FEW1% VC. R: Correlation Coefficient.

Figure 9:
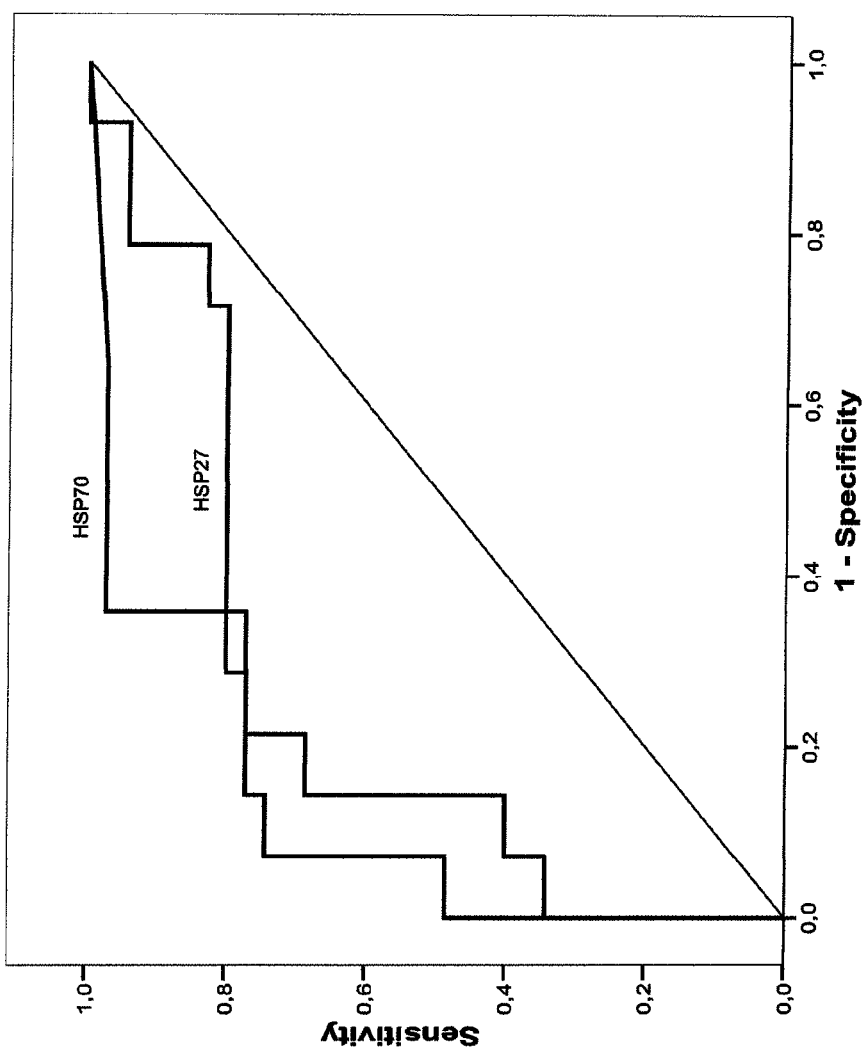

FIG. 9 shows a receiver operating characteristic (ROC) curve indicating sensitivity and specificity of HSP27 and HSP70 to diagnose COPD in the smoking study population.

EXAMPLES

Example 1

Materials and Methods

Patients

A total number of 64 patients were included in this case control study. Healthy volunteers (n=15), smokers without COPD (n=14), patients with mild to moderate COPD (n=19) and patients with severe or very severe COPD (n=16) were evaluated in four study groups. Patient characteristics are depicted in table 1.

TABLE 1

Clinical characteristics (severity of airflow obstruction
was determined using lung function test [LFT] in all subjects;
COPD patients meeting the GOLD diagnostic criteria for COPD).
Data are given as mean (+/- standard deviation) if not otherwise stated.

| Subject Category | Healthy | Healthy Smoker | COPD GOLD I-IV | COPD GOLD I & II | COPD GOLD III & IV |
|---|---|---|---|---|---|
| N | 15 | 14 | 35 | 19 | 16 |
| Male/Female | 10/5 | 7/7 | 20/15 | 10/9 | 10/6 |
| Age | 57.20 | 56.64 | 59.60 | 60.68 | 58.31 |
| Lung Function | | — | | | |
| FVC (L) | 4.55 | 3.84 | 2.80 | 3.33 | 2.14 |
| FEV1 (%) | 105.37 | 94.40 | 52.76 | 70.21 | 30.67 |
| FEV1/VC (%) | 76.80 | 75.95 | 51.18 | 61.74 | 37.80 |
| MEF 50 (%) | 100.67 | 87.64 | 27.29 | 39.42 | 11.93 |
| MEF 25 (%) | 103.53 | 75.71 | 29.71 | 37.37 | 20.00 |
| Smoking History | | | | | |
| Never-smoker | 15 | 0 | 0 | 0 | 0 |
| Ex-smoker | 0 | 3 | 7 | 4 | 3 |
| Current-smoker | 0 | 11 | 28 | 15 | 13 |
| Pack Years | 0 | 34 (25.2) | 45.8 (30.6) | 47.3 (29.7) | 44.0 (32.6) |
| Body Weight (kg) | 71.6 (13.9) | 76.4 (8.6) | 80.4 (21.6) | 79.7 (16.7) | 81.1 (27.2) |
| Body Height (cm) | 172.710.9) | 168.7 (8.1) | 169.2 (10.5) | 167.7 (12.1) | 171.2 (7.9) |

Abbreviations used: COPD: Chronic obstructive pulmonary disease,
FEV1: Forced expiratory volume in one second;
FVC: Forced vital capacity,
GOLD: Global Initiative for chronic obstructive lung disease
MEF: Maximum expiratory flow.

Exclusion criteria were acute exacerbation as defined by the guidelines of the WHO and the Global Initiative for Chronic Obstructive Lung Disease (GOLD; www.goldcopd.com) or use of immunomodulatory drugs within the past 14 days, history of asthma, autoimmune diseases, other relevant lung diseases (e.g., lung cancer, known a1-antitrypsin deficiency), or any known cardiopulmonary co-morbidity. Height and weight (Seca; Vogel and Halke, Germany) were measured and the body mass index (BMI) was determined. Pulmonary function parameters (FEV1, FVC, FEV1:FVC ratio) were measured using the same model spirometer (AutoboxV6200, SensorMedics, Austria). Measurements were made before and—if criteria for airflow obstruction were met—15-30 minutes after inhaling of 200 μg salbutamol. Arterial blood gases ($PaO_2$, $PaCO_2$) were obtained at rest while breathing room air in a sitting position. Measurement of arterial blood gases was performed with an ABL 510 gas analyzer (Radiometer, Denmark). Results are expressed as absolute values and as percentages of predicted values for age, sex and height, according to the European Community for Steel and Coal prediction equations (Quanje P H et al. Eur Respir J Suppl 16 (1993): 5-40). Predicted normal values were derived from the reference values of the Austrian Society of Pulmonary Medicine (Harnoncourt K et al., Österreich Ärztetg. 37 (1982): 1640-1642). Blood samples were collected at the time of pulmonary evaluation. Serum was acquired after centrifugation and aliquots were kept frozen at −20° C. until further testing.

Quantification of Caspase-Cleaved Cytokeratin-18 (ccCK-18)

Levels of cytokeratin-18 neo-epitope M30 were measured in samples using the M30-Apoptosense ELISA (Peviva, Sweden). In short, this ELISA uses a antibody, recognizing a neo-epitope exposed after apoptosis-induced cleavage of cytokeratin-18. M30 antigen levels can be measured in units per liter (U/L)—1 U/L is equivalent to 1.24 pmol of a synthesized peptide of the M30 recognition motif—according to the manufacturer. The sensitivity of the ELISA was stated to be 25 U/L. Within assay and between assay reproducibility were <10%. Serum concentrations were calculated by comparing OD values of the samples to OD values of the standard dilutions.

Evaluation of Serum Histone-Associated-DNA-Fragments

A commercial ELISA kit was used (Roche Applied Science, Germany) to quantify serum content of histone-DNA complexes. Samples were co-incubated in 96-well Microtitration plates with biotin-conjugated mouse monoclonal anti-histone antibody (clone H11-4) and peroxidase-conjugated mouse monoclonal anti-DNA antibody (clone MCA-33) for two hours at room temperature. After washing the wells, ABTS solution was added to each well. Enzyme reaction was monitored until sufficient color development was achieved and plates were read at 405 nm. OD values were calculated by subtracting OD values of blank wells from the mean of the sample wells.

Quantification of Serum Caspase-1/ICE

A commercially available enzyme-linked immunosorbent assay (ELISA) (BenderMedSystems, Austria) was used to determine serum contents of soluble caspase-1/ICE in serum samples. Microtitration plates pre-coated with monoclonal antibody to human ICE were incubated with sample material or diluted standard concentrations (400 pg/ml-6.25 pg/ml, seven dilution steps) at room temperature for 1.5 hours. Plates were washed three times with wash buffer and polyclonal rabbit ICE antiserum was added for 30 minutes. After another washing step, horseradish-peroxidase-conjugate was applied for 30 minutes. Wells were washed, and TMB substrate solution was used for the detection of enzyme activity. The reaction was stopped using sulphuric acid (2N). Plates were read at 450 nm on a Wallac Multilabel counter 1420 (PerkinElmer, USA). Concentrations were calculated by comparing optical density (OD) values of samples with OD of known concentrations of the standards.

Quantification of Interleukin-1 Receptor 4/ST2

A commercially available enzyme-linked immunosorbent assay (ELISA) (R&D Systems, USA) was used to determine serum contents of Interleukin-1 Receptor 4/ST2 (ST2) in our samples. Microtitration plates were pre-coated with a capture antibody against human ST2. Plates were then washed and blocked. Samples and standard dilutions (2000 pg/ml to 31.25 pg/ml) were incubated at room temperature. A biotinylated goat anti-human IL-1 R4 antibody was used for detection. TMB substrate solution was used for the detection of enzyme activity after addition of streptavidin conjugated to horseradish-peroxidase. The reaction was stopped using sulphuric acid (1N). Plates were read at 450 nm on a Wallac Multilabel counter 1420 (PerkinElmer, USA). Concentrations were calculated by comparing optical density (OD) values of samples with OD of known concentrations of the standards.

Quantification of Interleukin-10

ELISA technique (BenderMedSystems, Austria) was used to quantify levels of interleukin-10 (IL-10) in serum samples obtained after centrifugation of whole blood. 96-well plates were coated with a monoclonal antibody directed against the specific antigen and incubated over night at 4° C. After a washing step, plates were blocked with assay buffer for two hours. Following another washing step, samples and standards with defined concentrations of antigen were incubated as described by the manufacturer. Plates were then washed and incubated with enzyme-linked polyclonal antibodies. TMB substrate solution was applied after the appropriate time of incubation and another washing step. Color development was then monitored using a Wallac Multilabel counter 1420 (PerkinElmer, USA). The O.D values obtained were compared to the standard curve calculated from O.D. values of standards with known concentrations of antigen.

Statistical Methods

SPSS Software (SPSS Inc., USA) was used to calculate all results. A p-value <0.05 was considered statistically significant. Pair wise comparisons between groups were performed using the Mann-Whitney-U-Test. Correlations were calculated using the Spearman-Correlation-Coefficient. Results were not corrected for multiple testing.

Results

Figure 1:
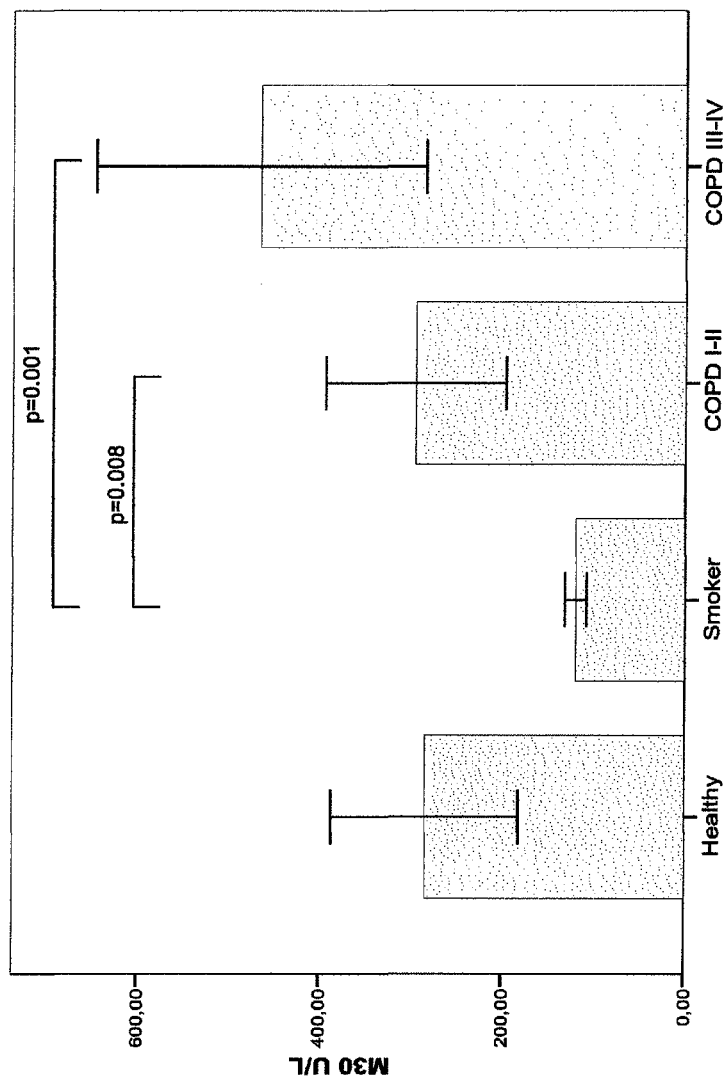
FIG. 1 shows serum concentrations of soluble apoptosis—specific caspase-cleaved cytokeratin-18—detected by using an antibody M30 (+/−SEM).

Apoptosis-Induced Caspase-Cleaved Cytokeratin-18 was Increased in Patients with COPD Elevated serum levels of M30 neo-epitope in patients with COPD I&II (294.96 U/L [87.81-502.11], p=0.008) and COPD III&IV (464.86 U/L [79.69-850.03], p=0.001) compared to serum contents of healthy smokers (119.67 U/L [93.85-145.49]) were shown. Healthy controls showed slightly increased levels of M30 (284.08 U/L [64.26-503.90], but this difference was not statistically significant (FIG. 1).

Figure 2:
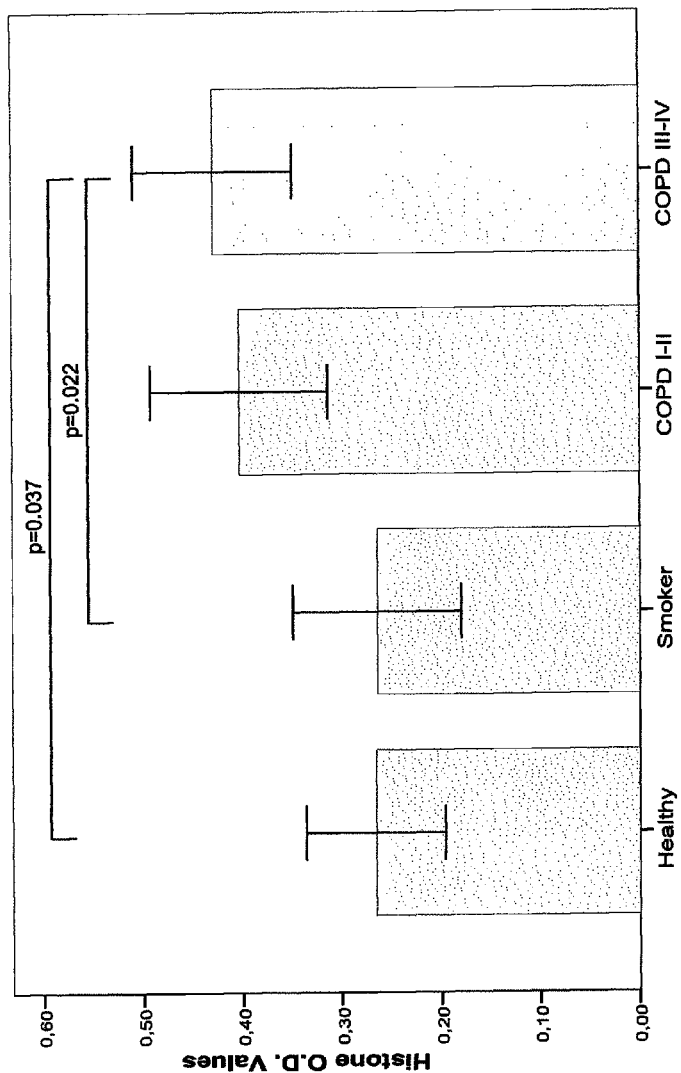
FIG. 2 shows the measured optical density (O.D.) values of circulating histone-associated-DNA fragments in serum samples (+/−SEM).

Content of Histone-Associated-DNA-Fragments was Augmented in Patients with Severe or Very Severe COPD The mean OD value in patients with COPD III&IV was determined at 0.43 [0.26-0.60]. This level was statistically significant different to histone levels in sera of healthy controls (0.27 [0.12-0.42], p=0.037) and smokers without COPD (0.26 [0.08-0.45], p=0.022). Patients with COPD I&II had elevated levels of serum histone-associated-DNA-fragments (0.40 [0.22-0.59]), though there was no statistical effect compared to other groups (FIG. 2).

Serum Caspase-1/ICE Levels Showed No Statistically Significant Difference

Figure 3:
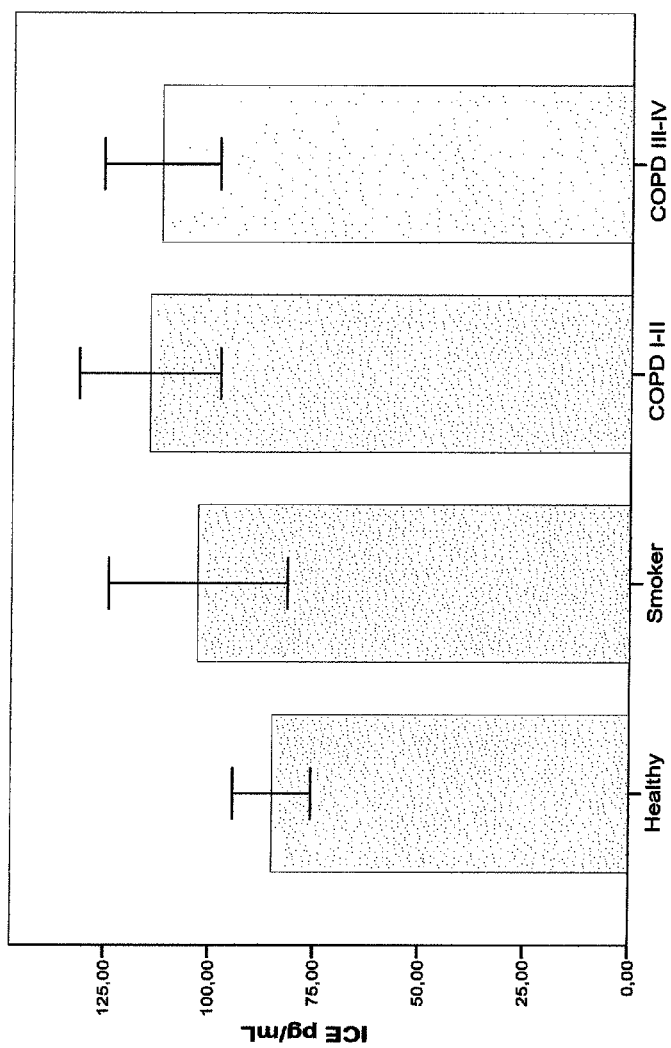
FIG. 3 shows the levels of caspase-1/ICE in peripheral serum samples of study patients (+/−SEM).

Concentrations of ICE in serum samples were 84.86 pg/ml ([64.85-104.87], 95% confidence interval [CI]) for healthy controls and 102.76 pg/ml [56.59-148.93] for smokers without COPD. Patients with COPD GOLD stage I&II showed a moderately higher mean content of 114.56 pg/ml [78.98-150.14], and patients with COPD III&IV had a mean serum level of 111.87 pg/ml [82.21-141.53] comparable to COPD I&II. There was no significant difference between any groups (FIG. 3).

Serum Levels of ST2 are Heightened in Patients with COPD

Figure 4:
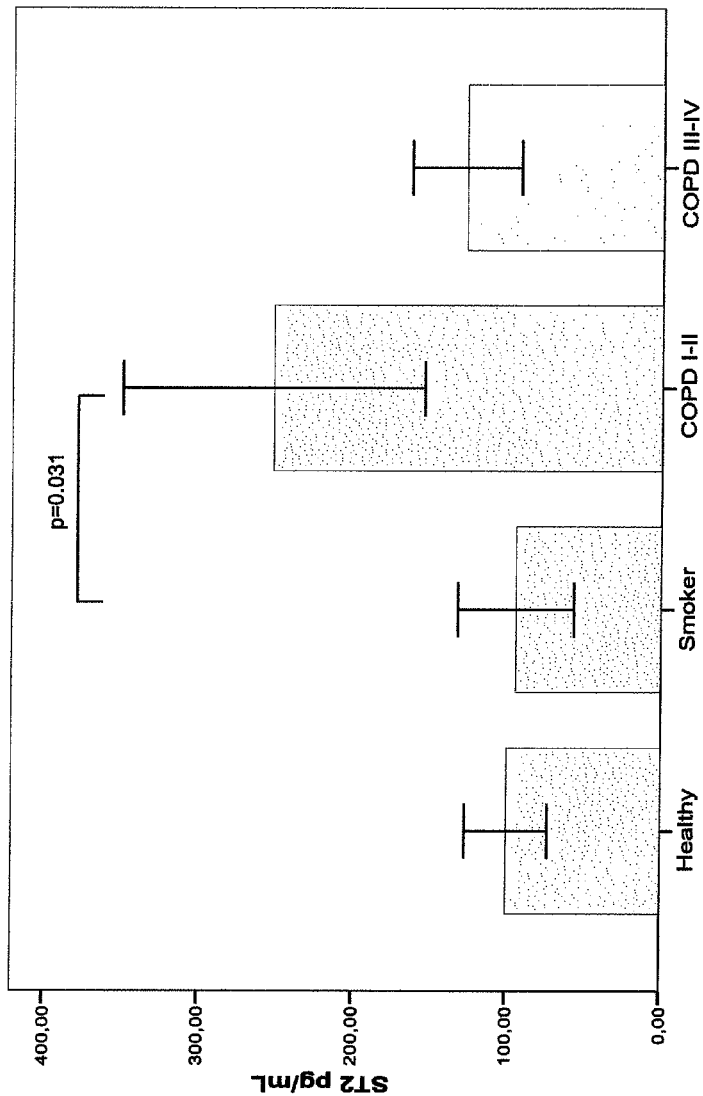
FIG. 4 shows the serum concentrations of soluble ST2 peaked in patients with COPD I&II (+/−SEM).

Elevated serum levels of ST2 in patients with COPD I&II (251.80 pg/ml [45.74-457.85], p=0.031) compared to serum contents of healthy smokers (94.01 pg/ml [11.57-176.46]) could be shown. All other group comparisons showed no significant differences; healthy controls (99.86 pg/ml [41.86-157.86]), COPD III&IV (127.24 pg/ml [51.72-202.75]) (FIG. 4).

Serum IL-10 Levels Showed No Statistically Significant Difference

Concentrations of IL-10 in serum samples were 8.84 pg/ml ([−6.14-23.81]) for healthy controls and 10.25 pg/ml [−3.84-24.34] for smokers without COPD. Patients with COPD GOLD stage I&II showed a content of 11.57 pg/ml [−8.49-31.62], and patients with COPD III&IV had a lower mean serum level of 0.63 pg/ml [−0.71-1.97]. There was no significant difference between any groups (FIG. 5).

Conclusion

Figure 6A:
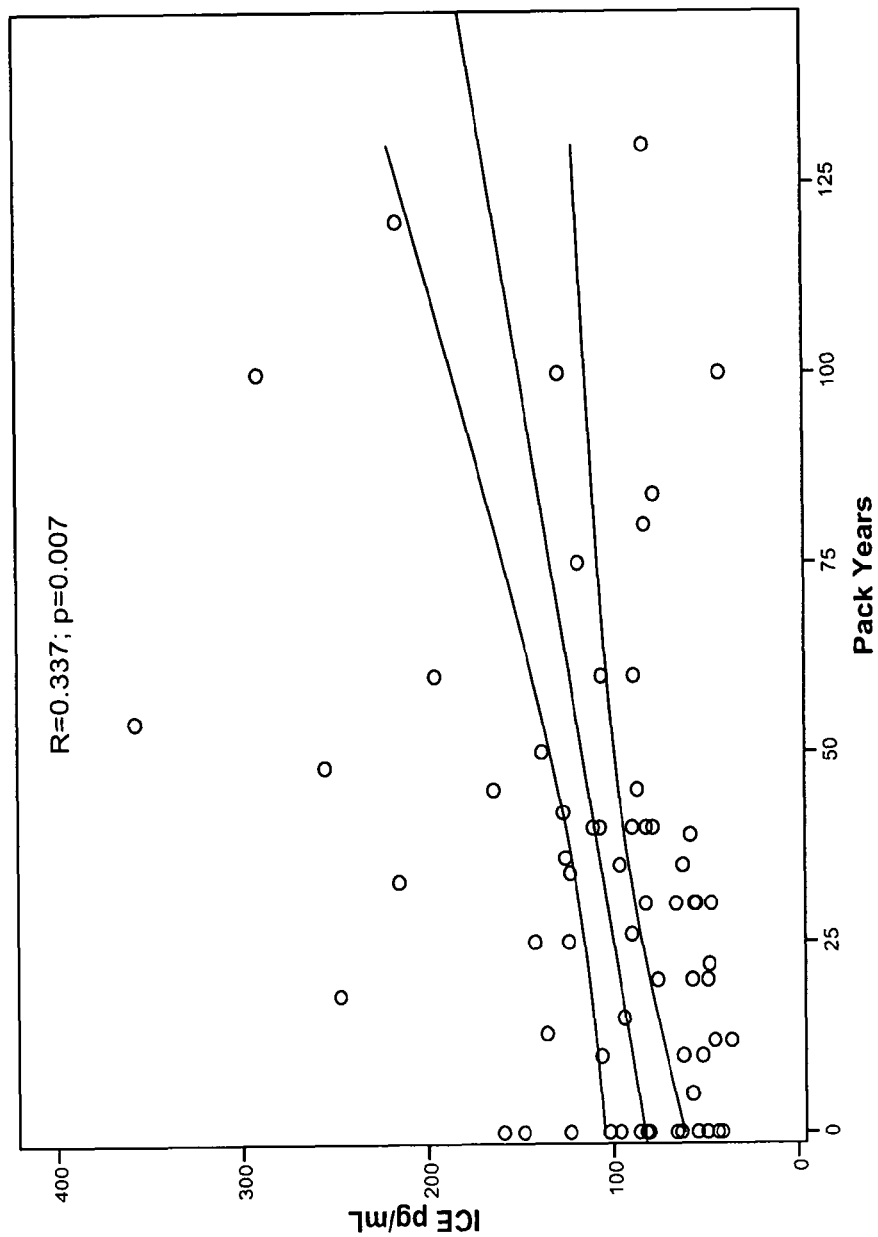
Figure 6B:
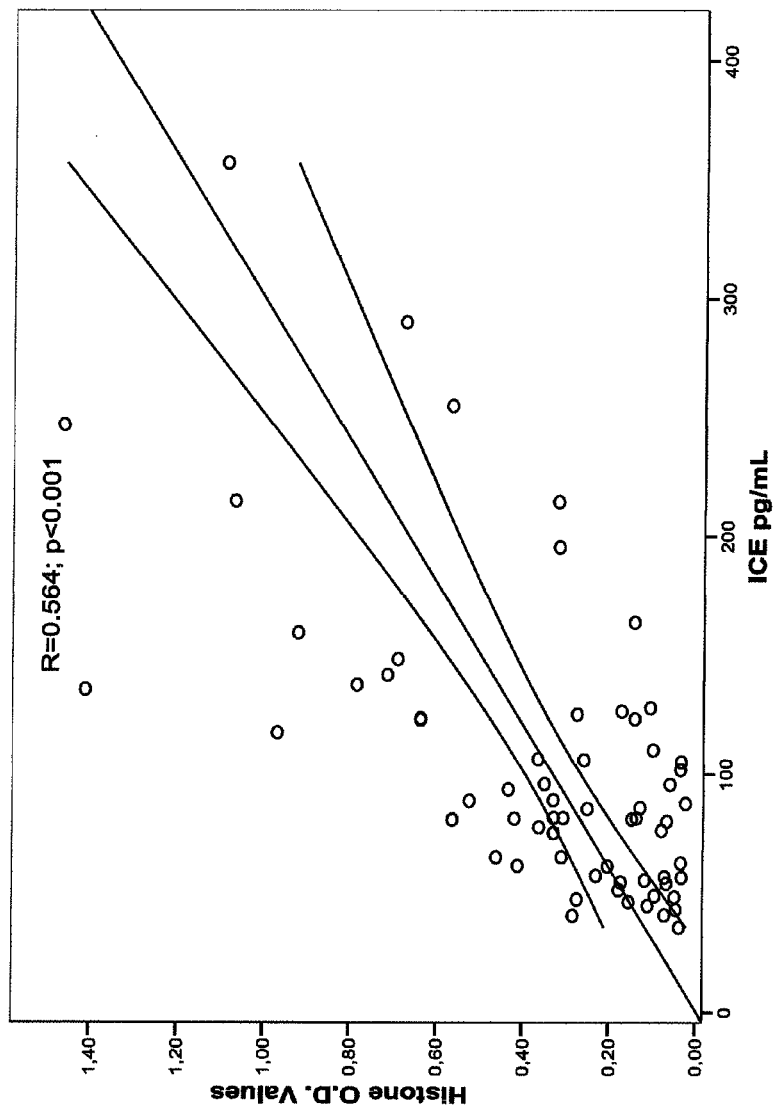

Chronic obstructive pulmonary disease is characterized by chronic inflammation of lung tissue and concomitant affection of other organ systems. This process is thought to be mainly triggered through numerous years of tobacco smoking. A strong correlation between the number of pack-years and serum concentration of pro-inflammatory caspase-1 ICE (ICE) indicating a direct effect of smoking habits on the systemic inflammatory response could be shown (FIG. 6A). Elevated levels of apoptosis-specific soluble ccCK-18 and histone-associated-DNA-fragments (histones) could be found in patients with COPD GOLD I&II and GOLD III&IV (FIGS. 1, 2). Serum contents of biological active protein ICE correlated significantly with levels of histones (FIG. 6B). In apoptotic cells, endonucleosome activation results in cleavage of DNA and generates long chromatin fragments, H1-rich short oligonucleosomes and mono-nucleosomes—termed histones—which are not attached to the nucleus. The release of apoptosis-specific histone-DNA-complexes seems to be a result of constant remodelling due to immune activation.

Figure 6C:
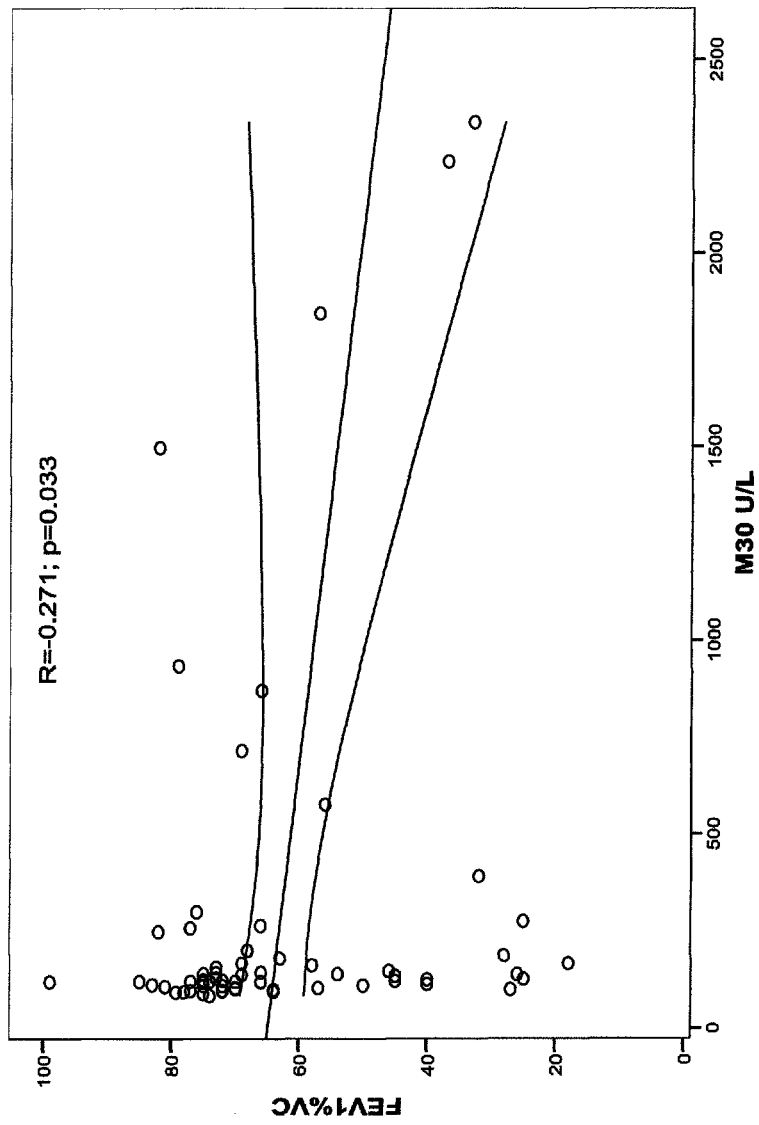
Figure 6D:
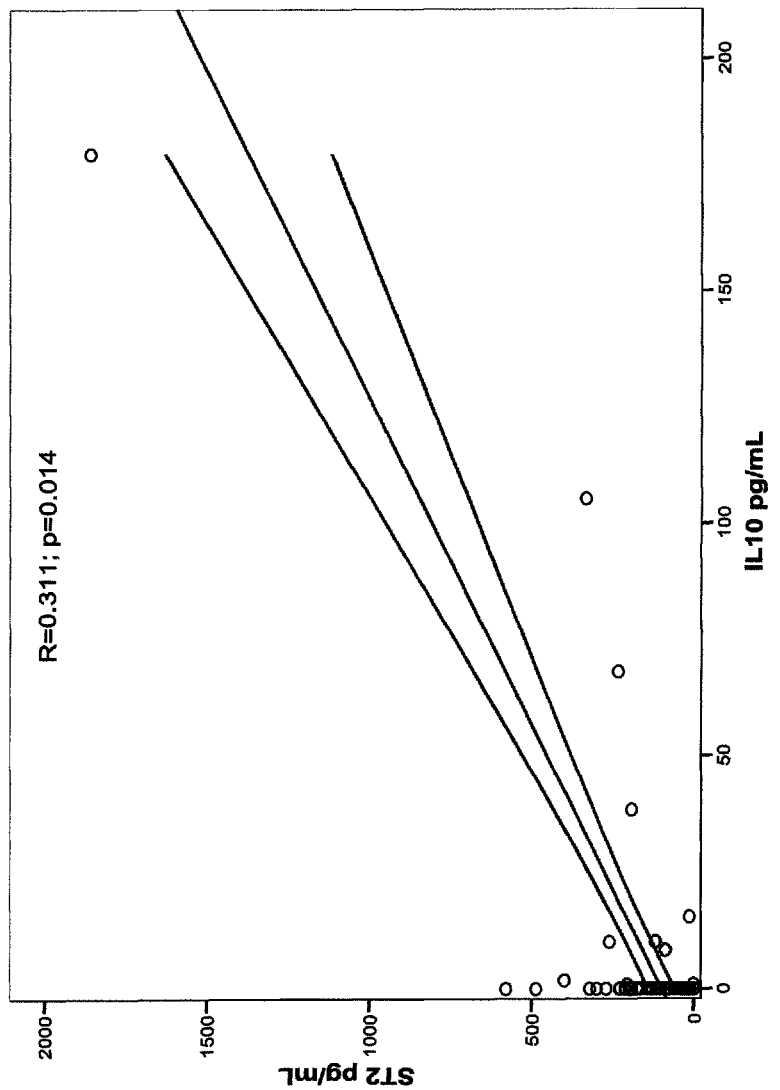

Pathogenesis of COPD is associated with degeneration of lung tissue due to increased activation and pro-apoptotic signalling of the innate and adaptive immune system in disease susceptible patients. Chronic inflammation leads to increased levels of ICE, a protease with Cys285 serving as the catalytic residue, that cleaves the 21 kDa biological inactive IL-1β precursor at Asp116-Ala117 to generate the 17.5 kDa mature form of IL-β. The active enzyme consists of two non-identical subunits (p10 and p20), both of which are essential for enzymatic activity, and therefore play a pivotal role in the apoptosis of various cells, including endothelial and epithelial cells. Apoptotic turnover results in liberation of cellular intermediate filaments such as cytokeratin-18 (CK-18). CK-18 is a major component of intermediate filaments and is widely expressed by epithelial and endothelial tissues. In apoptotic cells, CK-18 is phosphorylated and microfilaments aggregate rapidly. Different conditions of cellular stress increase cytoplasmatic microfilament reorganization as well as altered CK-18 polymerization. Consequently, caspase-mediated cleavage of CK-18 occurs during apoptosis and leads to formation of a specific neo-epitope, recognizing by the antibody M30. The binding-specificity of this antibody is restricted to apoptotic CK-18 degeneration products (caspase-cleaved CK-18 [ccCK-18]). Interestingly, the presence of soluble ccCK-18 was associated with impairment of lung function according to classification of COPD using the GOLD guidelines (FIG. 6C).

The above data indicate an apoptosis dependent lung degeneration in serum samples. Cleavage of cytokeratin-18 and release of ccCK-18 into the blood flow occurs with progression of the disease and can be used to monitor morbidity of the patient.

Previous studies have demonstrated a predominance of TH1 cytokine milieu in COPD patients. Since inflammation is always accompanied by secretion of proteins known to have anti-inflammatory properties, such as IL-10, another protein known to be related to the innate immune system named T1/ST2 was investigated. This soluble molecule is thought to modulate the TH1/TH2-associated immune responses. A significant increment of anti-inflammatory ST2 serum levels in patients with COPD I&II, but not in severe COPD, was observed. These observations indicate that COPD evidences increased makers of innate immune activation and regulation similar to autoimmune diseases, sepsis and lung specific diseases like fibrosis and asthma.

Recent work has shown that Toll-like receptors (TLRs) function as mammalian pattern-recognition receptors signalling the presence of microbial components to the innate immune cells. At least 10 members of the mammalian TLR family have been reported, with each TLR showing a distinct specificity for molecular pattern of microbes. Binding of activation ligands—e.g. lipopolysaccharide (LPS)—to TLRs induces activation of the NF-κB, leading to the production and release of pro-inflammatory cytokines. It is commonly accepted that pre-exposure to LPS reduces the sensitivity to a second challenge with LPS resulting in a diminished production of numerous cytokines both in rodents and humans. The molecular mechanisms of TLR-induced tolerance may involve the down regulation of the TLR4-MD2 complex which may lead to diminished TLR signalling. Furthermore, expression of IRAK-M and IRAK-1 as well as suppressor of cytokine signalling (SOCS-1) was shown to be related to endotoxin tolerance.

Several studies suppose an important role for the Toll/IL-1 receptor (TIR) family member ST2 in the induction of endotoxin tolerance. ST2 is expressed by TH2 cells, mast cells and macrophages. It was shown to be up-regulated after LPS stimulation and regulates cytokine expression in a model of acute lung injury. The secretion of ST2 in the initiation of COPD acts as a negative regulator of TLR4 and IL-1R signalling via sequestration of MyD88. In the clinical context this may mean that systemic T1/ST2 is functioning as protective serum protein in order to prohibit lung destruction due to over-active adaptive and innate immune system. Relevant to this finding was the observation that T1/ST2 correlated significantly with serum IL-10 levels in studies patient cohorts.

The results indicate that patients with COPD evidence increased apoptotic turnover and release of ccCK-18 and histone-DNA-complexes in the systemic blood flow. It was further found increased soluble T1/ST2 in patients with COPD I&II compared to healthy smokers. Increased levels of anti-inflammatory ST2 at early stages of COPD may be a possible negative feedback-loop to control the chronic inflammatory response. Moreover it could be shown that soluble ICE correlated significantly with history of smoking (pack years) indicating triggering of inflammation due to noxious inhalants. The identified serum markers serve to identify patients at risk for development and progression of COPD.

Example 2

Materials and Methods

Patients

The pool of patients used in this example was identical to the pool of patients used in example 1.

Heat Shock Proteins 27, 60, and 70

Levels of HSP27, HSP60, and HSP70 were determined using adapted enzyme-linked immunosorbent assay (ELISA) kits for the quantification of intracellular HSP (Duoset IC; R&D Systems, USA). Ninety-six-well microtiter plates were coated overnight at 4° C. with the capture antibody at a concentration of 1 μg/ml After blocking of plates, serum samples and standard protein in different concentrations were added to the wells. After a washing step, a biotin-labelled antibody was added to each well and incubated for 1 hour. Plates were washed and Streptavidin-HRP was added. Color reaction was achieved using tetramethylbenzidine (TMB; Sigma, USA) and was stopped by an acid stop solution. Optical density was measured at 450 nm on an ELISA reader.

Heat Shock Protein 90alpha

Serum levels of HSP90alpha were measured with a commercially available ready-to-use ELISA kit (Stressgen, USA). In brief, serum samples and standards were incubated in 96-well microtiter plates, precoated with antihuman HSP90 antibody. After a washing step, anti-HSP90: HRP-conjugated antibody was added, and plates were incubated for 24 hours. Plates were washed and TMB substrate was added. Color development was stopped by an acid stop solution, and optical density was determined at 450 nm. The amount of protein in each sample was calculated according to a standard curve of optical density values constructed for known levels of HSP90. The sensitivity of the ELISA has been determined to be 50 pg/ml; the intra-assay variability is stated to be less than 10% by the manufacturer.

20S Proteasome

Microtiter plates were incubated overnight at 4° C. with a monoclonal antibody against the α6-subunit of the 20S proteasome (Biomol, USA). Plates were washed and blocked for 1 hour with 1% BSA in phosphate-buffered saline. Serum samples and different concentrations of a standard protein (Biomol) were added, then plates were sealed and incubated for 24 hours at 4° C. A rabbit polyclonal antibody to 20S proteasome α/β subunits (Biomol), serving as the detection antibody, was added; and after a washing step, plates were incubated with a peroxidase-labeled donkey antirabbit IgG (Jackson ImmunoResearch, United Kingdom) for another 2 hours. Tetramethylbenzidine served as color substrate. The reaction was stopped by adding 1N sulphuric acid. Plates were read at 450 nm using a Wallac Multilabel counter 1420 (PerkinElmer, USA).

Interleukin-6

Serum levels of IL-6 were determined by a commercially available ELISA kit (BenderMedSystems, Austria). Assays were performed according to the manufacturer's instructions. Plates were read at 450 nm on an ELISA reader, and IL-6 contents were calculated comparing optical density values of samples with optical density values of known IL-6 concentrations.

Statistical Methods

SPSS Software (SPSS Inc., USA) was used to calculate all results. A p-value <0.05 was considered statistically significant. Pair wise comparisons between groups were performed using the Mann-Whitney-U-Test. Correlations were calculated using the Spearman-Correlation-Coefficient.

Results

HSP27

Figure 7A:
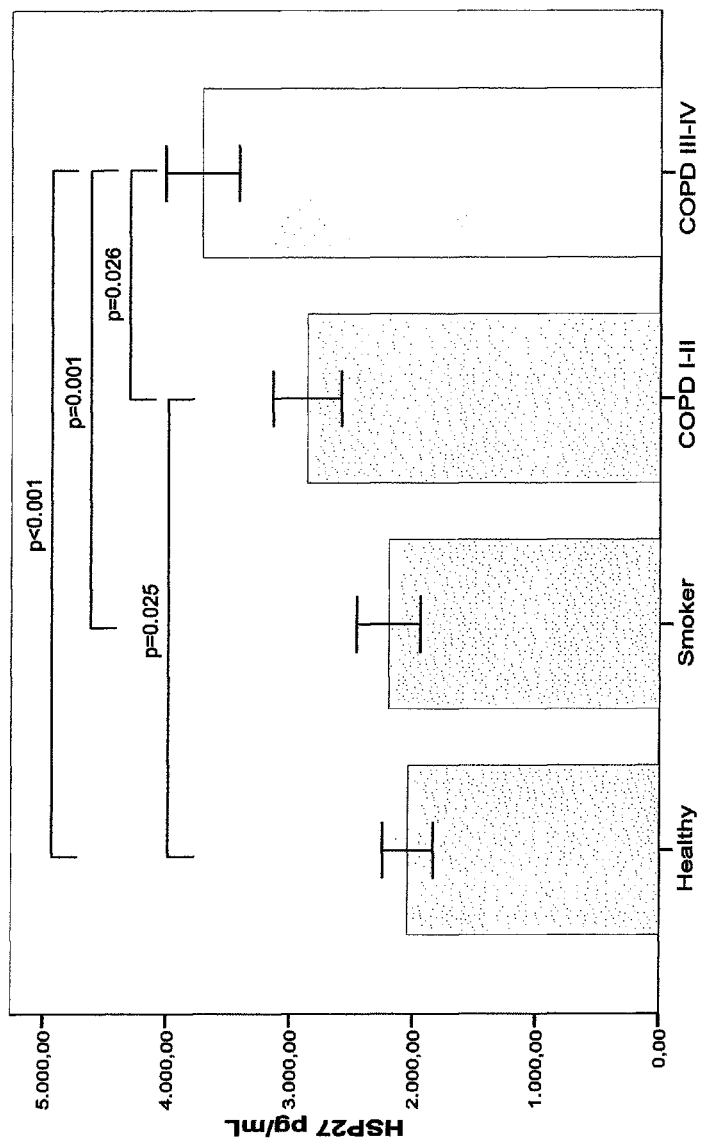

Serum levels of HSP27 were 2042.57 pg/ml [1599.58-2485.57] (mean [95% confidence interval]) in healthy controls, 2199.64 [1641.52-2757.75] in healthy smokers, 2862.62 [2280.49-3444.74] in COPD GOLD I-II, and 3717.58 [3079.35-4355.81] in COPD GOLD III-IV. Statistically significant differences were found between healthy controls and COPD I-II (p=0.025), healthy controls and COPD III-IV (p<0.001), healthy smokers and COPD III-IV (p=0.001), and COPD I-II and COPD III-IV (p<0.001) (FIG. 7a).

HSP60

Figure 7B:
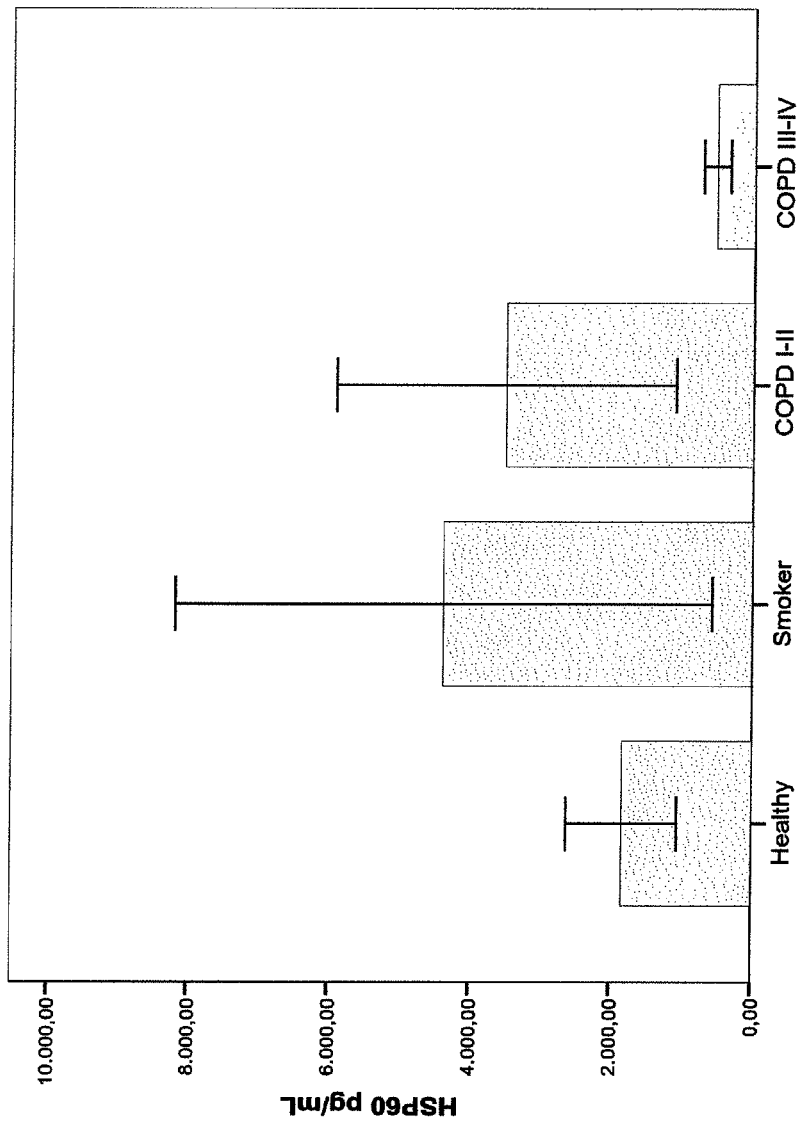

Serum levels of HSP60 were 1836.69 pg/ml [153.30-3520.08] in healthy controls, 4378.40 [−3851.48-12608.28] in healthy smokers, 3497.42 [−1561.38-8556.23] in COPD GOLD I-II, and 531.81 [132.57-931.05] in COPD GOLD III-IV. No statistically significant differences were found between the groups (FIG. 7b).

HSP70

Figure 7C:
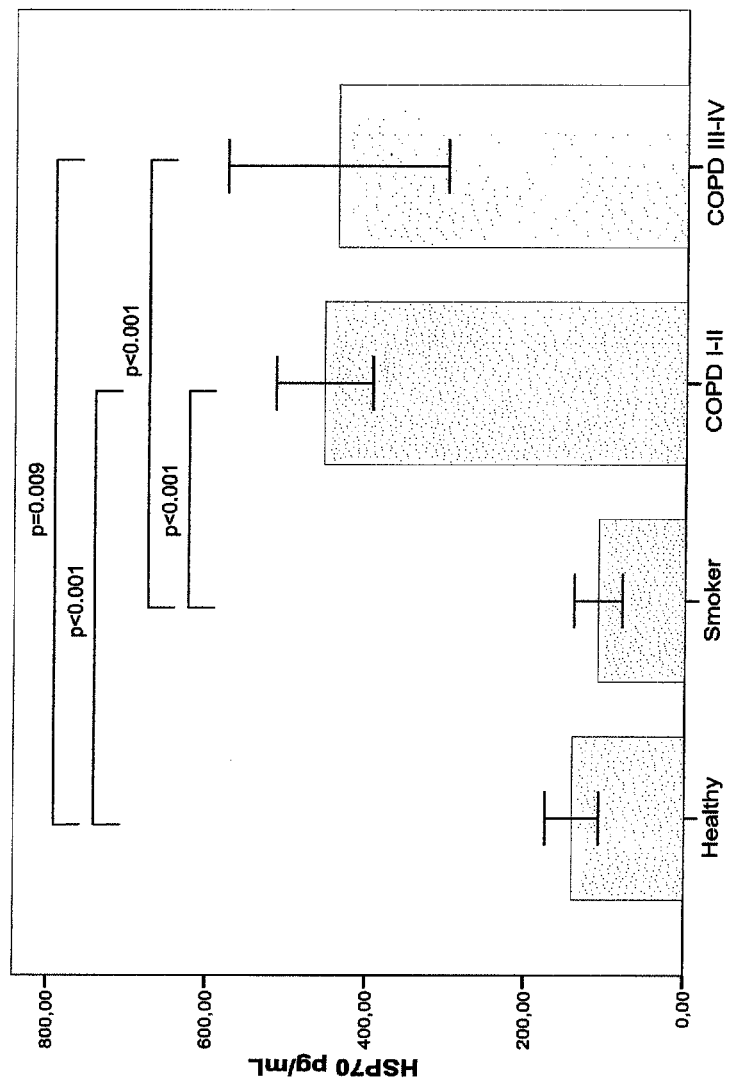

Serum levels of HSP70 were 140.50 pg/ml [67.97-213.04] in healthy controls, 108.50 [43.30-173.69] in healthy smokers, 454.29 [327.05-581.52] in COPD GOLD I-II, and 437.92 [143.41-732.42] in COPD GOLD III-IV. Statistically significant differences were found between healthy controls and COPD I-II (p<0.001), healthy controls and COPD III-IV (p=0.009), healthy smokers and COPD I-II (p<0.001), and healthy smokers and COPD III-IV (p<0.001) (FIG. 7c).

HSP90alpha

Figure 7D:
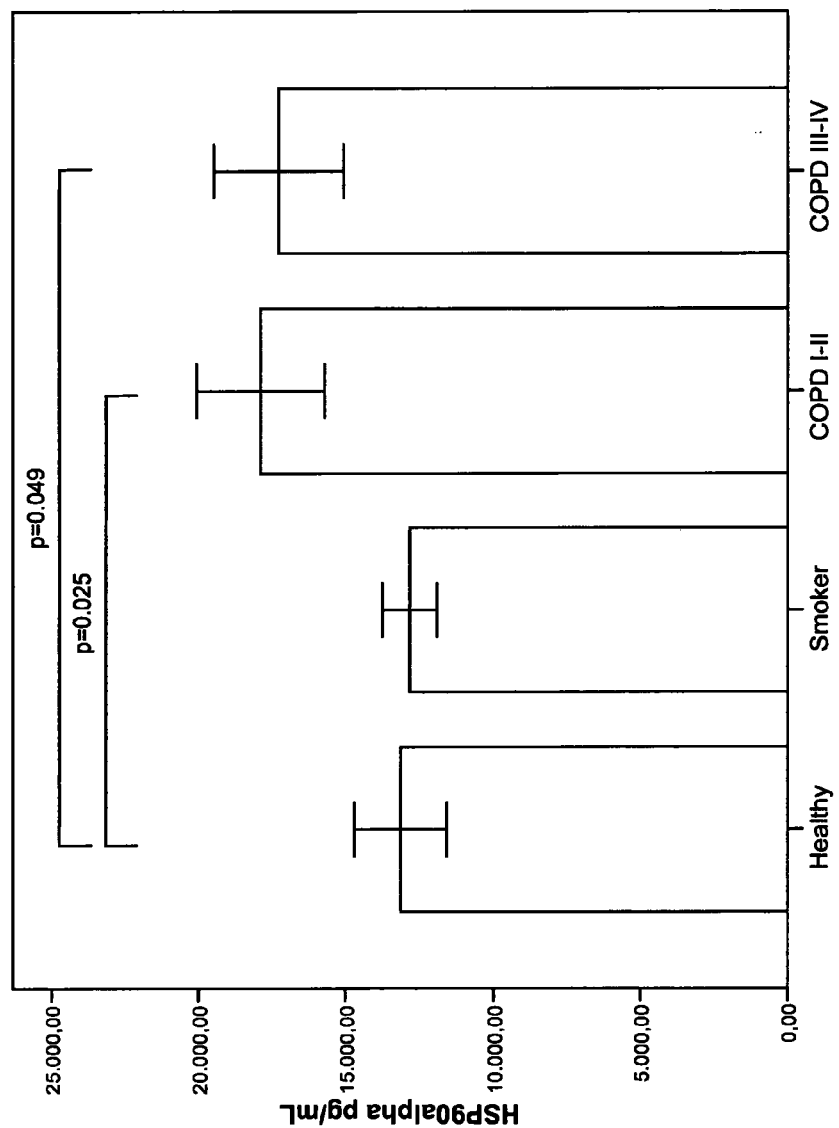

Serum levels of HSP90alpha were 13133.78 pg/ml [9791.40-16476.15] in healthy controls, 12827.91 [10838.21-14817.62] in healthy smokers, 17884.50 [13307.14-22461.85] in COPD GOLD I-II, and 17273.02 [12573.96-21972.08] in COPD GOLD III-IV. Statistically significant differences were found between healthy controls and COPD I-II (p=0.025), and healthy controls and COPD III-IV (p=0.049) (FIG. 7d).

20S Proteasome

Figure 7E:
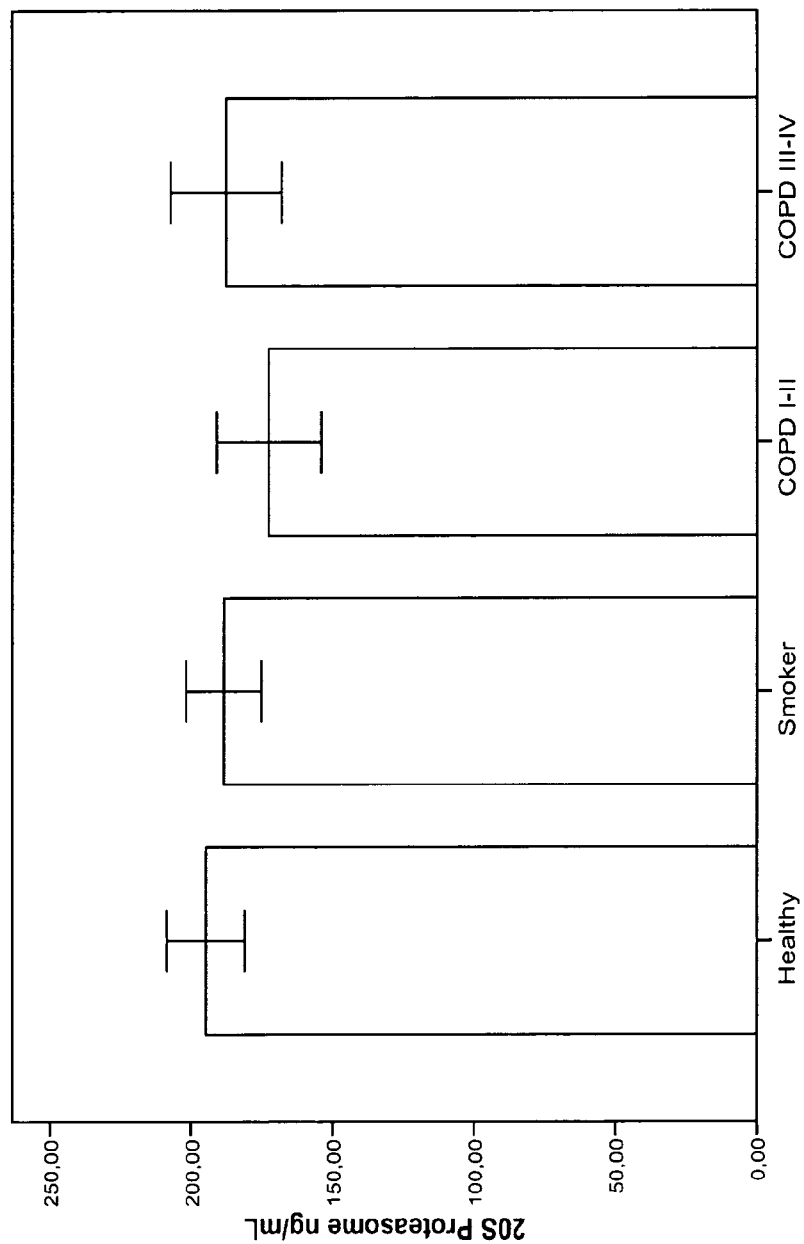
Figure 7F:
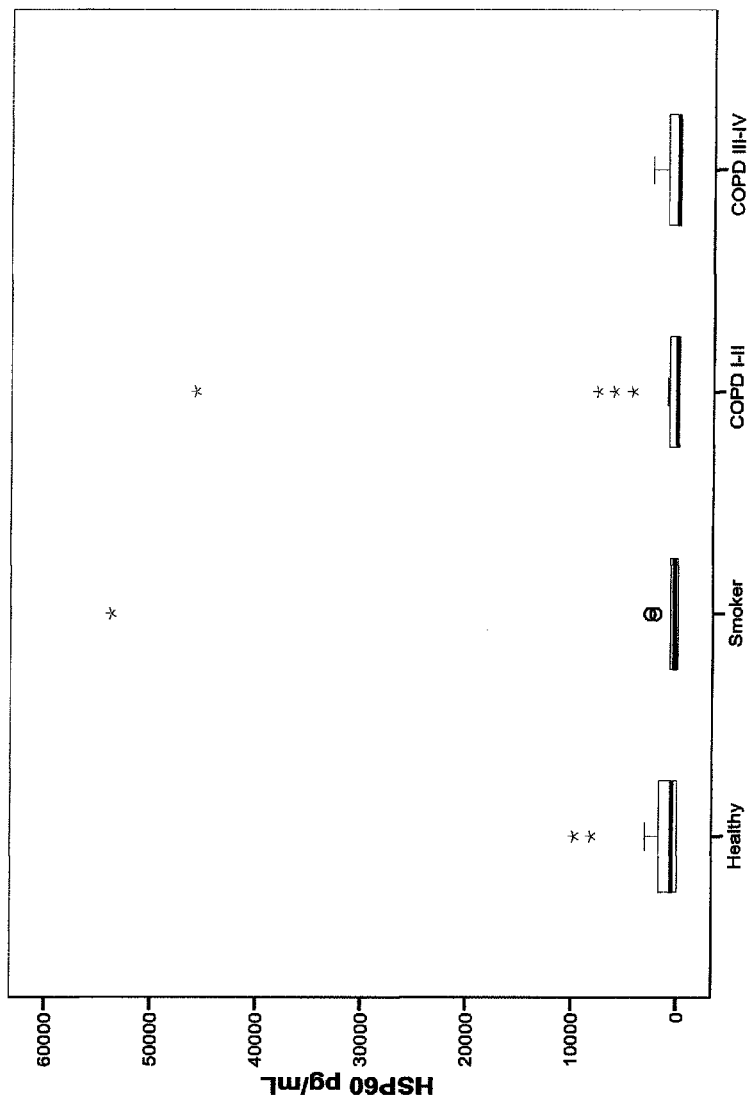
Figure 8A:
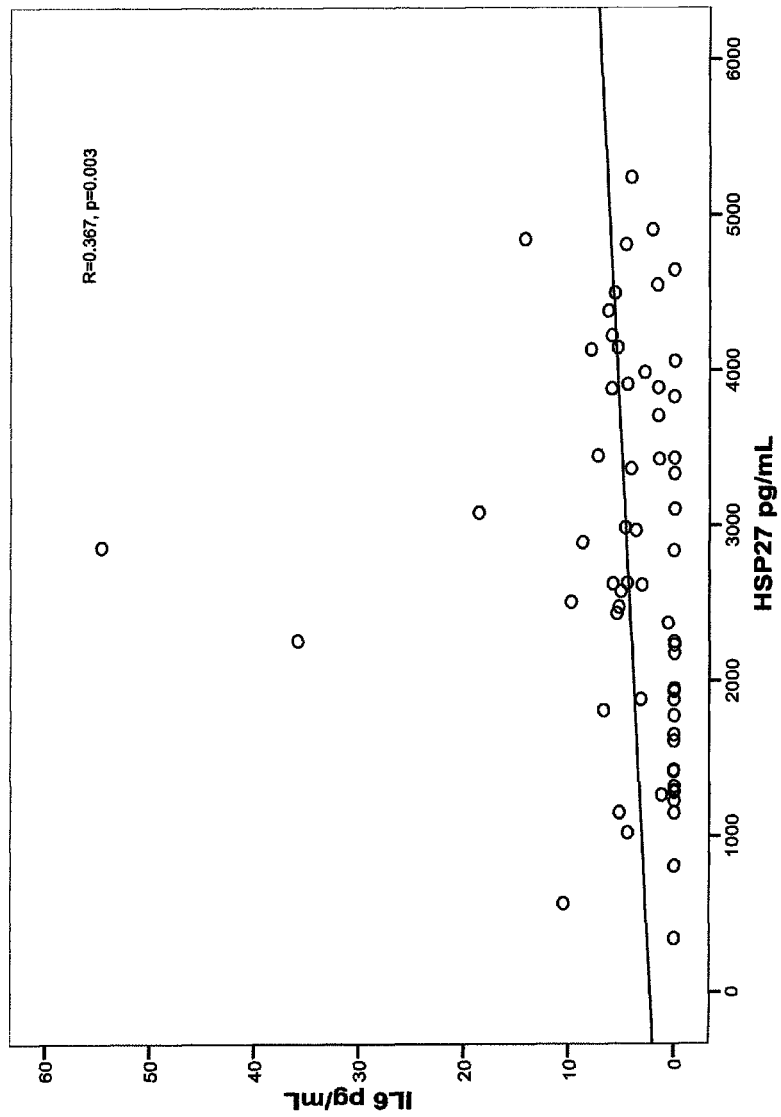
Figure 8B:
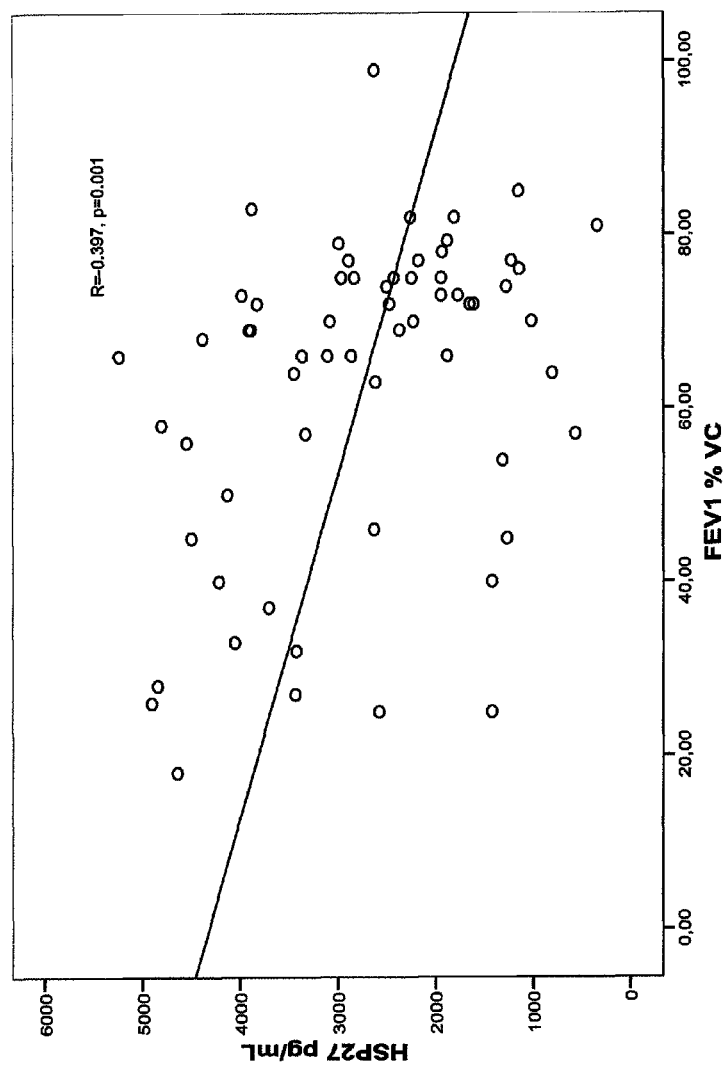
Figure 8C:
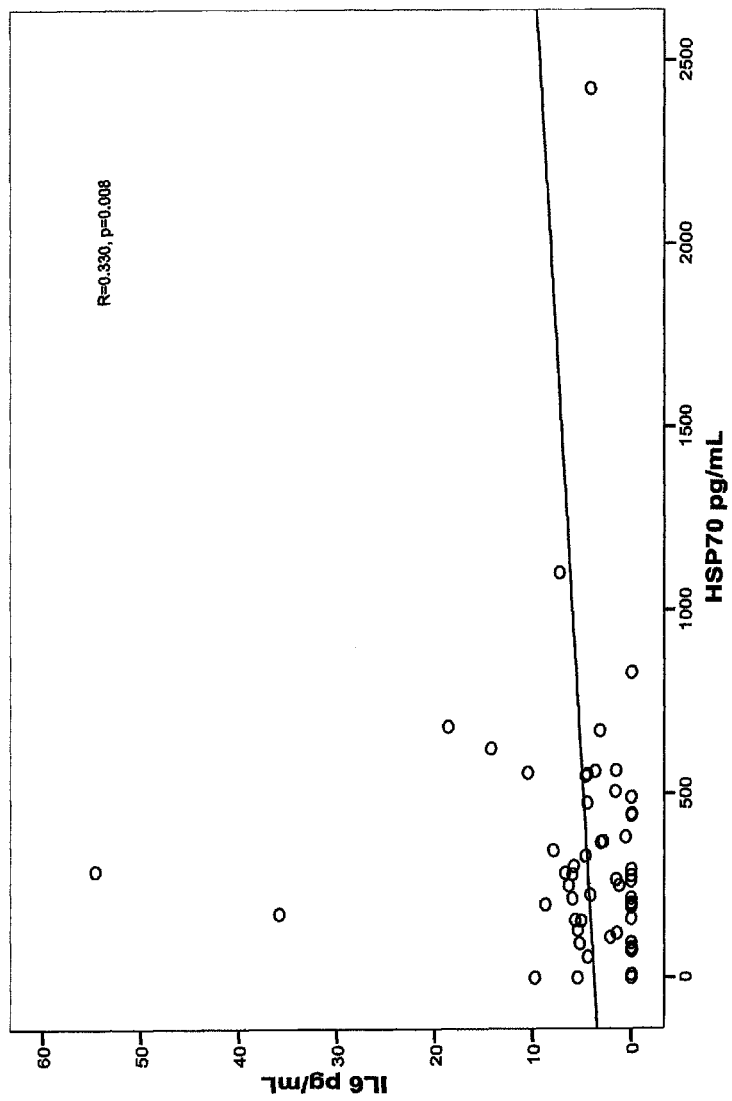
Figure 8D:
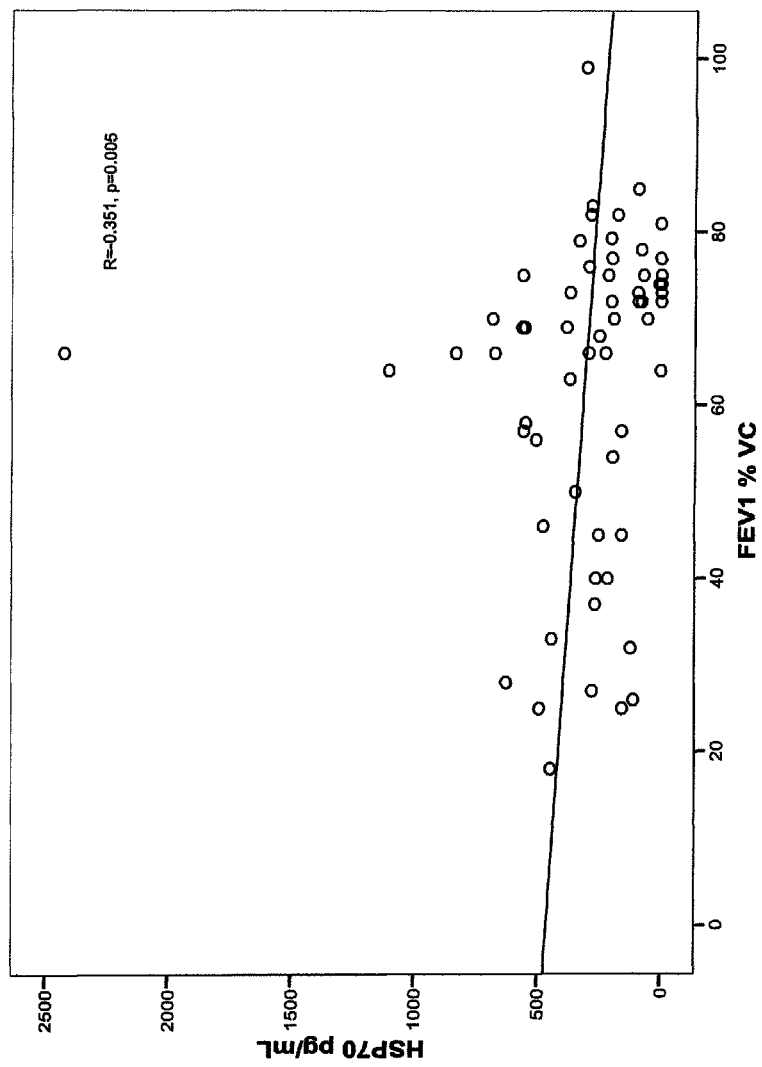

Serum levels of 20S proteasome were 194.78 ng/ml [164.94-224.62] in healthy controls, 188.25 [159.26-217.25] in healthy smokers, 172.33 [133.78-210.88] in COPD GOLD I-II, and 187.50 [145.54-229.46] in COPD GOLD III-IV. No statistically significant differences were found between the groups (FIG. 7e).

Interleukin-6

Serum levels of IL-6 were 5.18 pg/ml [0.17-10.19] in healthy controls, 1.65 [−0.11-3.42] in healthy smokers, 7.14 [1.19-13.09] in COPD GOLD I-II, and 2.99 [0.99-5.00] in COPD GOLD III-IV. A statistically significant difference was found between healthy smokers and COPD I-II (p=0.017).

Correlations and Regression Models

Correlations between HSPs, FEV1% VC and IL-6 are presented in FIGS. 8a to 8d. In univariate logistic regression models including only healthy smokers and patients with COPD, HSP27 had an area under the curve (AUC) in the receiver operating characteristic (ROC) curve of 0.763 (0.624-0.902: 95% Cl; p=0.004), and HSP70 showed an AUC of 0.885 (0.786-0.983: 95% Cl; p<0.001). All other variables showed no significant result in the univariate logistic regression analysis (FIG. 9).

CONCLUSION

Patients suffering from chronic obstructive pulmonary disease present progressive inflammation of the bronchial airways, small airways, and lung parenchyma. Lung biopsies revealed massive infiltration of the peribronchial tissue with neutrophils, macrophages, and lymphocytes as part of the innate and adaptive immune system. Activation of these cells is believed to lead to remodelling of the lung tissue. The slowly progressive process of tissue remodelling is accompanied by a significant amount of cellular destruction. In COPD, both endogenous factors including neutrophils and cytotoxic T-cells as well as exogenous stimuli like tobacco smoke are thought to contribute towards tissue destruction. However, cessation of smoking does not alter impairment of the inflammatory response.

The induction of inflammatory signals and increased cellular turnover result in upregulation of intracellular heat shock proteins and augmented release into the extracellular environment. In this example a significant increase of HSP27 in serum samples taken from the peripheral blood flow of patients suffering from COPD as compared to healthy smokers could be shown. HSP27 functions as repair mechanism aiming at the stability and correct posttranslational folding of intracellular proteins as well as the prevention of apoptotic cell death. Elevated serum levels of HSP27 were reported in inflammatory disorders including acute coronary syndrome and chronic allograft nephropathy. Expression of HSP27 is transiently induced as a response to stress events. Termination of the acute triggering results in an immediate downregulation of HSP27 concentrations to normal levels. Thus, HSP27 is only upregulated when its cytoprotective properties are required. Interestingly the results demonstrate a continuous increase of serum HSP27 concentrations with disease severity and a strong correlation with serum pro-inflammatory IL-6. This effect may be due to increased tissue devastation especially in late stages of COPD and spreading of the inflammatory disease to other organ systems resulting in a systemic spillage of HSP27 into the vascular bed. HSP27 generally acts as anti-apoptotic mediator and can be seen as an endogenous immunosuppressive attempt to control excessive inflammation in the clinical setting of COPD. Furthermore, serum content of HSP27 showed high sensitivity and specificity to determine the occurrence of COPD in a logistic regression model.

The role of extracellular HCP60 has not been well defined. The data provided herein do not provide any support for HSP60 being a key element in the pathogenesis of COPD. Serum concentrations of HSP60 did not correlate with levels of other HSPs.

Serum levels of HSP70 were elevated in patients in early and late GOLD stages of COPD. A four-fold increase in the GOLD I-II group compared to non-symptomatic smokers was evidenced. HSP70 is an intracellular chaperone that is released into the extracellular space upon cell death or by means of various secreting pathways. Extracellular HSP70 has been reported to activate cells of the innate and adaptive immune system and to stimulate cytokine production. Increased concentrations of soluble HSP70 in COPD samples were found. Values peaked in the COPD I-II group indicating a state of vast immune activation primarily at the early stages of the disease. Furthermore, levels of HSP70 correlated significantly with levels of HSP27, HSP90alpha and IL-6 and are thus part of the systemic "danger signal" accompanying the immune activation in COPD. Furthermore, serum content of HSP27 showed high sensitivity and specificity to determine the occurrence of COPD in a logistic regression model.

Soluble HSP90alpha was significantly upregulated in the peripheral blood flow in the COPD groups as compared to healthy non-smokers. Elevated levels of HSP90alpha have previously been described in on-pump coronary artery bypass grafting and wound healing after hypoxia. HSP90 was also characterised as central factor in antigen presentation to T lymphocytes via major histocompatibility complex class II molecules (MHCII). In synopsis with the data, it is concluded that elevated levels of extracellular HSP90alpha in COPD are an essential elicitor of the adaptive immune system, triggering a possible autoreactive response to self-antigen. This function of HSP90alpha may also change the immunogenicity of the associated antigen. Therefore, HSP90alpha has immunomodulatory effects through cross-presentation of associated peptides in the context of major histocompatibility complex molecules.

The extracellular serum content of 20S proteasome was not statistically increased or decreased in the investigated study cohorts. Levels remained under 200 ng/mL in all groups and appear to be of subordinate importance in the progression of COPD.

Summarizing elevated serum concentrations of soluble immune modulatory heat shock proteins 27, 70 and 90alpha in patients with COPD could be demonstrated. This spillage into the vascular bed is at least partly caused by continuous activation of the immune system in the deterioration of COPD through endogenous and exogenous trigger mechanisms. Furthermore, HSP27 and HSP70 showed excellent statistical trends to serve as diagnostic markers for the detection of airway obstruction at early states of COPD.

The invention claimed is:

1. A method for diagnosing chronic obstructive pulmonary disease (COPD) in a human subject or the risk of a human subject to develop COPD comprising the steps of:
    providing a sample from a human subject,
    determining the amount of caspase-cleaved cytokeratin-18 (ccCK-18), histones, heat shock protein 27 (HSP27), heat shock protein 70 (HSP70) and/or heat shock protein 90 alpha (HSP90 alpha) in said sample,
    diagnosing COPD when the amount of ccCK-18, histones, HSP27, HSP70 and/or HSP90 alpha is increased compared to the amount of ccCK-18, histones, HSP27, HSP70 and/or HSP90 alpha in healthy human subjects, or
    diagnosing the risk to develop COPD when the amount of ccCK-18, histones and/or HSP70 is reduced compared to the amount of ccCK-18, histones and/or HSP70 in healthy human subjects.

2. The method according to claim 1, characterised in that further the amount of interleukin-1 receptor 4 (ST2) is determined, wherein COPD is diagnosed when the amount of ST2 is increased compared to the amount of ST2 in healthy human subjects or wherein the risk to develop COPD is diagnosed when the amount of ST2 is reduced compared to the amount of ST2 in healthy human subjects.

3. The method according to claim 1, characterised in that the sample is blood, serum or plasma.

4. The method according to claim 1, characterised in that the amount of interleukin-1 receptor 4 (ST2), caspase-cleaved cytokeratin-18 (ccCK-18), histones, heat shock protein 27 (HSP27), heat shock protein 70 (HSP70) and/or heat shock protein 90 alpha (HSP90 alpha) is determined by an immunoassay selected from the group consisting of enzyme-linked immunosorbent assay (ELISA), radioimmunoassay (RIA) and Western Blot.

5. The method according to claim 1, characterised in that the amount of interleukin-1 receptor 4 (ST2) in blood samples of a healthy human subject ranges preferably from 50 to 150 pg/ml, preferably 60 to 140 pg/ml, more preferably 70 to 130 pg/ml.

6. The method according to claim 1, characterised in that the amount of caspase-cleaved cytokeratin-18 (ccCK-18) in blood samples of a healthy human subject ranges from 200 to 350 U/l, preferably from 200 to 330 U/l, more preferably from 250 to 300 U/l, measured as cytokeratin-18 new epitope M30.

7. The method according to claim 1, characterised in that the amount of histones in blood samples of a healthy human subject is 20 to 50% lower, preferably 25 to 40% lower, than in blood samples of a human subject suffering from COPD.

8. The method according to claim 1, characterised in that the amount of heat shock protein 27 (HSP27) in blood samples of a healthy human subject ranges form 1500 to 2000 pg/ml, preferably from 1600 to 2400 pg/ml, more preferably from 1700 to 2300 pg/ml.

9. The method according to claim 1, characterised in that the amount of heat shock protein 70 (HSP70) in a blood samples of a healthy human subject ranges from 50 to 200 pg/ml, preferably from 70 to 190 pg/ml, more preferably from 80 to 180 pg/ml.

10. The method according to claim 1, characterised in that the amount of heat shock protein 90 alpha (HSP90 alpha) in a blood samples of a healthy human subject ranges from 10,000 to 15,000 pg/ml, preferably from 11,000 to 14,500 pg/ml, more preferably from 12,000 to 14,000 pg/ml.

11. The method according to claim 1, characterised in that COPD is diagnosed when the amount of interleukin-1 receptor 4 (ST2), caspase-cleaved cytokeratin-18 (ccCK-18), histones, HSP27, HSP70 and/or HSP90 alpha in the sample is at least 10%, preferably at least 20%, increased compared to the amount of ST2, ccCK-18, histones, HSPO27, HSP70 and/or HSP90 alpha in healthy human subjects.

12. The method according to claim 1, characterised in that the risk to develop COPD is diagnosed when the amount of interleukin-1 receptor 4 (ST2), caspase-cleaved cytokeratin-18 (ccCK-18), histones, HSP27, HSP70 and/or HSP90 alpha in the sample is at least 10%, preferably at least 20%, reduced compared to the amount of ST2, ccCK-18, histones, HSP27, HSP70 and/or HSP90 alpha in healthy subjects.

13. A method for discriminating between COPD stage I/II and COPD stage III/IV in a human subject comprising the steps of:
    providing a sample from a human subject suffering from COPD,
    determining the amount of caspase-cleaved cytokeratin-18 (ccCK-18), histones, heat shock protein 27 (HSP27) and/or heat shock protein 70 (HSP70) in said sample,
    diagnosing COPD stage I/II when the amount of ccCK-18, histones, and/or HSP27 is reduced compared to the amount of ccCK-18, histones and/or HSP27 determined in a sample from a human subject suffering from COPD stage III/IV and/or when the amount of HSP70 is increased compared to the amount of HSP70 determined in a sample from a human subject suffering from COPD stage III/IV, or
    diagnosing COPD stage III/IV when the amount of ccCK-18, histones and/or HSP27 is increased compared to the amount of ccCK-18, histones and/or HSP27 determined in a sample from a human subject suffering from COPD stage I/II and/or when the amount of HSP70 is reduced compared to the amount of HSP70 determined in a sample from a human subject suffering from COPD stage I/II.

14. The method according to claim 13, characterised in that further the amount of interleukin-1 receptor 4 (ST2) is determined, wherein COPD stage I/II is diagnosed when the amount of ST2 is increased compared to the amount of ST2 determined in a sample from a human subject suffering from COPD stage III/IV, or wherein COPD stage III/IV is diagnosed when the amount of ST2 is reduced compared to the amount of ST2 determined in a sample from a human subject suffering from COPD stage I/II.

15. A method for monitoring the progress of chronic obstructive pulmonary disease (COPD) in a human subject comprising the steps of:
   providing a sample from a human subject,
   determining the amount of caspase-cleaved cytokeratin-18 (ccCK-18), histones, heat shock protein 27 (HSP27) and/or heat shock protein 70 (HSP70) in said sample,
   comparing the amount of ccCK-18, histones, HSP27 and/or HSP70 in the sample of said human subject with the amount of ccCK-18, histones, HSP27 and/or HSP70 in a sample from said human subject determined in an earlier sample of said human subject.

* * * * *

UNITED STATES PATENT AND TRADEMARK OFFICE
CERTIFICATE OF CORRECTION

PATENT NO. : 8,415,112 B2
APPLICATION NO. : 12/999291
DATED : April 9, 2013
INVENTOR(S) : Jan Hendrik Ankersmit It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this
Eighth Day of October, 2013

Teresa Stanek Rea
*Deputy Director of the United States Patent and Trademark Office*